United States Patent
Bel Aiba et al.

(10) Patent No.: US 10,526,382 B2
(45) Date of Patent: Jan. 7, 2020

(54) HUMAN NEUTROPHIL GELATINASE-ASSOCIATED LIPOCALIN (HNGAL) MUTEINS CAPABLE OF BINDING ANGIOPOIETIN-2 (ANG-2) AND METHODS OF USE THEREOF

(71) Applicant: Pieris Pharmaceuticals GmbH, Freising-Weihenstephan (DE)

(72) Inventors: Rachida SIham Bel Aiba, Munich (DE); Andrea Allersdorfer, Wolnzach (DE); Alexander Wiedenmann, Ulm (DE); Christine Rothe, Dachau (DE); Shane Olwill, Freising (DE); Hendrik Gille, Berlin (DE); Laurent Audoly, Toulouse (FR)

(73) Assignee: Pieris Pharmaceuticals GmbH, Freising-Weihenstephan (DE)

( * ) Notice: Subject to any disclaimer, the term of this patent is extended or adjusted under 35 U.S.C. 154(b) by 31 days.

(21) Appl. No.: 15/546,609

(22) PCT Filed: Jan. 27, 2016

(86) PCT No.: PCT/EP2016/051657
§ 371 (c)(1),
(2) Date: Jul. 26, 2017

(87) PCT Pub. No.: WO2016/120307
PCT Pub. Date: Aug. 4, 2016

(65) Prior Publication Data
US 2018/0016312 A1    Jan. 18, 2018

(30) Foreign Application Priority Data
Jan. 28, 2015    (EP) ..................... 15152826

(51) Int. Cl.
| C07K 14/47 | (2006.01) |
| C07K 14/515 | (2006.01) |
| A61K 38/17 | (2006.01) |
| A61K 45/06 | (2006.01) |
| G01N 33/74 | (2006.01) |

(52) U.S. Cl.
CPC .......... *C07K 14/47* (2013.01); *A61K 38/1709* (2013.01); *A61K 45/06* (2013.01); *C07K 14/515* (2013.01); *G01N 33/74* (2013.01); *C07K 2319/00* (2013.01); *C07K 2319/30* (2013.01); *C07K 2319/31* (2013.01)

(58) Field of Classification Search
CPC .. C07K 14/47; C07K 14/515; C07K 2319/00; C07K 2319/30; C07K 2319/31; G01N 33/74; A61K 45/06; A61K 38/1709
See application file for complete search history.

(56) References Cited

U.S. PATENT DOCUMENTS

| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | De Sauvage et al. |
| 6,696,245 B2 | 2/2004 | Winter et al. |
| 7,250,297 B1 | 7/2007 | Beste et al. |
| 7,252,998 B2 | 8/2007 | Skerra et al. |
| 9,051,382 B2 | 6/2015 | Trentmann et al. |
| 9,260,492 B2 | 2/2016 | Matschiner et al. |
| 9,549,968 B2 | 1/2017 | Skerra et al. |
| 9,884,898 B2 | 2/2018 | Corvey et al. |
| 2003/0069395 A1 | 4/2003 | Sato et al. |
| 2006/0058510 A1 | 3/2006 | Skerra et al. |
| 2006/0088908 A1 | 4/2006 | Skerra et al. |
| 2010/0159587 A1 | 6/2010 | Brinkmann et al. |
| 2013/0079286 A1 | 3/2013 | Skerra et al. |
| 2017/0114109 A1 | 4/2017 | Skerra et al. |
| 2017/0166615 A1 | 6/2017 | Matschiner et al. |
| 2017/0369542 A1 | 12/2017 | Trentmann et al. |
| 2018/0141988 A1 | 5/2018 | Hinner et al. |
| 2018/0148484 A1 | 5/2018 | Hinner et al. |

FOREIGN PATENT DOCUMENTS

| DE | 4417598 A1 | 12/1995 |
| DE | 19641876 A1 | 4/1998 |
| DE | 19742706 A1 | 4/1999 |
| DE | 19926068 C1 | 1/2001 |
| EP | 0 330 451 A2 | 8/1989 |
| EP | 0 361 991 A2 | 4/1990 |
| JP | 2005503829 A | 2/2005 |
| JP | 2007284351 A | 11/2007 |
| WO | WO-96/23879 A1 | 8/1996 |
| WO | WO-98/16873 A1 | 4/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |

(Continued)

OTHER PUBLICATIONS

"Chain A Crystal Structure of Siderocalin (Ngal, Lipocalin 2) Complexed With Trencam-3,2-Hopo, a Cepabactin Analogue," GenBank Accession No. 1X71_A, Sep. 24, 2008.

(Continued)

*Primary Examiner* — Robert S Landsman
(74) *Attorney, Agent, or Firm* — Brenda H. Jarrell; Brian E. Reese; Choate, Hall & Stewart, LLP

(57) ABSTRACT

The present disclosure provides hNGAL muteins that bind Ang-2 and can be used in various application including pharmaceutical applications, for example, to inhibit or reduce angiogenesis. The present disclosure also concerns methods of making one or more muteins described herein as well as compositions and combinations comprising one or more of such muteins. The present disclosure further relates to nucleic acid molecules encoding such muteins and to methods for generation of such muteins and nucleic acid molecules. In addition, the application discloses therapeutic and/or diagnostic uses of these muteins as well as compositions and combinations comprising one or more of such muteins.

Figure 1:
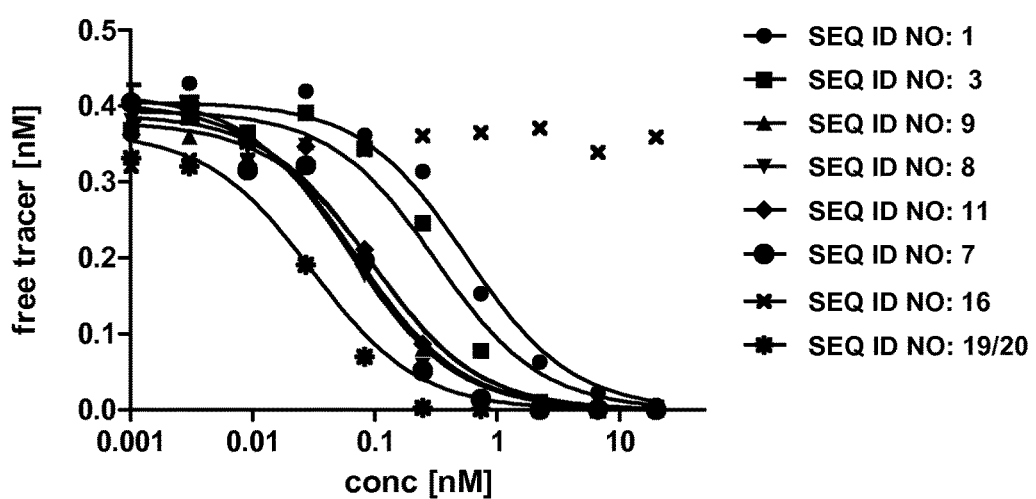

47 Claims, 5 Drawing Sheets
Specification includes a Sequence Listing.

(56) References Cited

FOREIGN PATENT DOCUMENTS

| WO | WO-03/029471 A1 | 4/2003 |
|---|---|---|
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2009/052390 A1 | 4/2009 |
| WO | WO-2009/156456 A1 | 12/2009 |
| WO | WO-2014/076321 A1 | 5/2014 |

OTHER PUBLICATIONS

Altschul, S. et al., Gapped BLAST and PSI-BLAST: a new generation of protein database search programs, Nucl. Acids Res.. 1997, 25(17):3389-3402.
Amstutz, P. et al., In vitro display technologies: novel developments and applications, Curr. Opin. Biotechnol., 2001, 12:400-405.
Bachmann, Barbara J., Linkage Map of *Escherichia coli* K-12. Edition 8, Microbial. Rev., Jun. 1990, 54(2):130-197.
Beck, et al., Nucleotide Sequence and Genome Organisation of Filamentous Bacteriophages f1 and fd, Gene, vol. 16, pp. 35-58, 1981.
Beste, G. et al., Small antibody-like proteins with prescribed ligand specificities derived from the lipocalin fold, Proc. Natl. Acad. Sci. USA, Mar. 1999, 96:1898-1903.
Bittker, J. et al., Nucleic acid evolution and minimization by nonhomologous random recombination, Nat. Biotechnol., Oct. 2002, 20:1024-1029.
Bos et al., OctoDEX.TM.—Controlled Release of Pharmaceutical Proteins from Hydrogels, Business Briefing: Pharmatech, 2003:1-6.
Breustedt, D. et al., Comparative ligand-binding analysis of ten human lipocalins, Biochim. Biophys. Acta, 2006, 1764:161-173.
Broders, O et al., Hyperphage. Improving antibody presentation in phage display, Methods Mol. Biol., 2003, 205:295-302.
Brody et al., Active and Passive Immunotherapy for Neurodegenerative Disorders, Annu. Rev. Neurosci., 2008, 31:175-193.
Bruckdorfer, T., et al., From Production of Peptides in Milligram Amounts for Research to Multi-Tons Quantities for Drugs of the Future, Curr. Pharm. Biotechnol., 2004, 5:29-43.
Bullock, W. et al., XL1-Blue: A High Efficiency Plasmid Transforming recA *Escherichia coli* Strain with Beta-Galactosidase Selection, Biotechniques, 1987, 5(4):376-378.
Bundgaard, J.R. et al., Molecular Cloning and Expression of a cDNA Encode NGAL: A Lipocalin Expressed in Human Neutrophils, Biochemical and Biophysical Research Communications, Aug. 15, 1994, pp. 1468-1475, vol. 202, No. 3, XP002036694.
Carnemolla et al., Phage Antibodies with PAN-Species Recognition of the Oncofoetal Angiogenesis Marker Fibronectin ED-B Domain, Int. J. Cancer, 1996, 68:397-405.
Chan et al., The primary structure of rat α 2μ globulin-related protein, Nucleic Acids Research, vol. 16, No. 23, pp. 11368, 1988.
Coles, et al., The Solution Structure and Dynamics of Human Neutrophil Gelatinase-associated Lipocalin, J. Mol. Biol., vol. 289, pp. 139-157, 1999.
Dennis, M. et al., Albumin Binding as a General Strategy for Improving the Pharmacokinetics of Proteins, J. Biol. Chem., Sep. 20, 2002, 277(38):35035-35043.
Dodel et al., Immunotherapy for Alzheimer's disease, Lancet Neurology, Apr. 2003, 2:215-220.
Ebbinghaus et al., Diagnostic and Therapeutic Applications of Recombinant Antibodies: Targeting the Extra-Domain B of Fibronectin, a Marker of Tumor Angiogenesis, Curr. Pharm. Des., 2004, 10:1537-1549.
Fitzgerald, Kevin, In Vitro Display Technologies—New Tools for Drug Discovery, Reviews, vol. 5, No. 6, pp. 253-258, Jun. 2000.
Fling, S. and Gregerson, D., Peptide and Protein Molecular Weight Determination by Electrophoresis Using a High-Molarity Tris Buffer System without Urea, Anal. Biochem., 1986, 155:83-88.
Flower, Darren R., The lipocalin protein family: structure and function, Biochem. J., 1996, 318:1-14.
Frank, Ronald, The SPOT-synthesis technique Synthetic Peptide arrays on membrane supports—principles and applications, J. Immunol. Methods, 2002, 267:13-26.
Fuerteges, F. and Abuchowski, A., The Clinical Efficacy of Poly(Ethylene Glycol)-Modified Proteins,: J. Control. Release, 1990, 11:139-148.
Fujii, Phage display and beyond antibody—molecular target by antibody molecule, Seikagaku, 2010, vol. 82, No. 8, pp. 710-726, Abstract.
Gaillard, P. et al., Diphtheria toxin receptor-targeted brain drug delivery, International Congress Series., 2005, 1277:185-198.
Gaillard, P. et al., Targeted delivery across the blood-brain barrier, Expert Opin Drug Deliv., 2005, 2(2):299-309.
Gasteiger et al., ExPASy: the proteomics server for in-depth protein knowledge and analysis, Nucleic Acids Res., 2003, 31(13):3784-3788.
Goetz, D. et al., Ligand Preference Inferred from the Structure of Neutrophil Gelatinase Associated Lipocalin, Biochemistry, 2000, 39:1935-1941.
Gronwall et al., Selection and characterization of Affibody ligands binding to Alzheimer amyloid β peptides, J. Biotechnol., 2007, 128:162-183.
Haass et al., Soluble protein oligomers in neurodegeneration: lessons from the Alzheimer's amyloid β-peptide, Nat. Rev. Mol. Cell. Biol., Feb. 2007, 8:101-112.
Hengen, Paul N., Methods and Reagents, Trends Biochem. Sci., vol. 21, pp. 75-76, 1996.
Hoess, Ronald H., Phage Display of Peptides and Protein Domains, Structural Biology, vol. 3, pp. 572-279, 1993.
Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Hortschansky et al., The aggregation Kinetics of Alzheimer's β-amyloid peptide is controlled by stochastic nucleation, Protein Sci., 2005, 14:1753-1759.
Hoyer, W. et al., Stabilization of a β-hairpin in monomeric Alzheimer's amyloid-β peptide inhibits amyloid formation, Proc. Natl. Acad. Sci. USA, Apr. 1, 2008, 105(13):5099-5104.
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lohrengel, B. et al., Expression and Purification of Woodchuck Tumour Necrosis Factor Alpha, Cytokine, vol. 12, No. 6, pp. 573-577, Jun. 2000.

(56) References Cited

OTHER PUBLICATIONS

Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Moretto et al., Conformation-sensitive Antibodies against Alzheimer Amyloid-β by Immunization with a Thioredoxin-constrained B-cell Epitope Peptide, J. Biol. Chem., 2007, 282(15):11436-11445.
Murakami, H. et al., Random insertion and deletion of arbitrary number of bases for codon-based random mutation of DNAs, Nat. Biotechnol., Jan. 2002, 20:76-81.
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between $α_1$-Acid Glycoprotein and Serum Retinol-Binding Protein and Its Relatives, 1987, Department of Biochemistry, University of Miami School of Medicine.
Pini et al., Design and Use of a Phage Display Library, J. Biol. Chem., Aug. 21, 1998, 273(34):21769-21776.
Pini, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A$^+$ and ED-B$^+$ Isoforms by Human and Experimental Colorectal Cancer, Am. J. Pathol., Feb. 1996, 148(2):579-592.
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. et al., A Novel Type of Receptor Protein, Based on the Lipocalin Scaffold, with Specificity for Digoxigenin, J. Mol. Biol., 2000, 297:1105-1120.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al., An engineered lipocalin specific for CTLA-4 reveals a combining site with structural and conformational features similar to antibodies, PNAS, May 19, 2009, 106(20):8198-8203.

Skerra, Arne, 'Anticalins': a new class of engineered ligand-binding proteins with antibody-like properties, J. Biotechnol., 2001, 74:257-275.
Skerra, Arne, Anticalins as alternative binding proteins for therapeutic use, Current Opinion in Molecular Therapeutics, 2007, 9(4):336-344.
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Skerra, S., et al., Lipocalins as a scaffold, Elsevier Science B.V., Biochimica et Biophysica Acta 1482, pp. 337-350, 2000.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.
Vajo, Z. and Duckworth, W., Genetically Engineered Insulin Analogs: Diabetes in the New Millenium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt, M. and Skerra, A., Construction of an Artificial Receptor Protein ("Anticalin") Based on the Human Apolipoprotein D, ChemBioChem, 5: 191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.
Wang et al., Expanding the genetic code, Chem. Comm., 2002, 1:1-11.
Wang, A. M. et al., Molecular Cloning of the Complementary DNA for Human Tumor Necrosis Factor, Science, vol. 228, pp. 149-154, 1985 (Abstract).
Wells, J. et al., Rapid Evolution of Peptide and Protein Binding Properties In Vitro, Current Opinion in Structural Biology, vol. 2, pp. 597-604, 1992.
Wilson, D. et al., The use of mRNA display to select high-affinity protein-binding peptides, Proc. Natl. Acad. Sci. USA, Mar. 27, 2001, 98(7):3750-3755.
Yanisch-Perron, C. et al., Improved M13 phage cloning vectors and host strains: nucleotide sequences of the M13mp18 and pUC19 vectors, Gene, 1985, 33:103-119.
Zaccolo, M. et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).
Database Geneseq "Human mature lipocalin 2 (NGAL) mutant protein I36M." XP002756088, retrieved from EBI accession No. GSP:BBG44509 sequence, Jul. 17, 2014.
Database Geneseq, "Human mature NGAL-tear lipocalin mutant fusion protein, SEQ 16.", XP002756094, retrieved from EBI accession No. GSP:BBG44294, Database accession No. BBG44294 sequence, Jul. 17, 2014.

(56) References Cited

OTHER PUBLICATIONS

Database Geneseq, "Human neutrophil gelatinase-associated lipocalin mutein, SEQ ID 2.", XP002756089, retrieved from EBI accession No. GSP:AXV25593, Database accession No. AXV25593 sequence, Apr. 1, 2010.
Hansen et al., "Effects of angiopoietins-1 and -2 on the receptor tyrosine kinase Tie2 are differentially regulated at the endothelial cell surface," Cellular Signalling, vol. 22, 2010, pp. 527-532.
International Search Report and Written Opinion issued in corresponding application No. PCT/EP2016/051657 dated Apr. 18, 2016.

SEQ ID NO: 8

SEQ ID NO: 7

HUMAN NEUTROPHIL GELATINASE-ASSOCIATED LIPOCALIN (HNGAL) MUTEINS CAPABLE OF BINDING ANGIOPOIETIN-2 (ANG-2) AND METHODS OF USE THEREOF

CROSS-REFERENCE TO RELATED APPLICATIONS

This application is a National Stage application of PCT/EP2016/051657, filed Jan. 27, 2016, which claims priority from European application EP 15152826.2, filed Jan. 28, 2015.

I. BACKGROUND

Angiogenesis, the formation of new blood vessels from existing ones, is essential to many physiological and pathological processes. Normally, angiogenesis is tightly regulated by pro- and anti-angiogenic factors, but in the case of diseases such as cancer, ocular neovascular diseases, arthritis, and psoriasis, the process can go awry. Folkman, J., Nat. Med., 1:27-31 (1995). There are a number of diseases known to be associated with deregulated or undesired angiogenesis. Such diseases include, but are not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid (or hematopoietic) tumors (such as leukemias and lymphomas). Other diseases associated with undesired angiogenesis will be apparent to those skilled in the art.

Although many signal transduction systems have been implicated in the regulation of angiogenesis, one of the best-characterized and most endothelial cell-selective systems involves the Tie-2 receptor tyrosine kinase that is selectively expressed within the vascular endothelium (referred to as "Tie-2" or "Tie-2R" (also referred to as "ORK"); murine Tie-2 is also referred to as "tek") and its ligands, the angiopoietins (Yancopoulos, G. D., et al., Nature 407 [2000] 242-48; Gale, N. W. and Yancopoulos, G. D., Genes Dev. 13:1055-1066 [1999]).

There are 4 known angiopoietins; angiopoietin-1 ("Ang-1," alternatively abbreviated with ANGPT1 or Ang1) through angiopoietin-4 ("Ang-4"). These angiopoietins are also referred to as "Tie-2 ligands" (Davis, S., et al., Cell, § 7:1161-1169 [1996]; Grosios, K., et al, Cytogenet Cell Genet, § 4:118-120 [1999]; Holash, J., et al, Investigative Ophthalmology & Visual Science, 42:1611-1625 [1999]; Koblizek, T. I., et al, Current Biology, S:529-532 [1998]; Lin, P., et al, Proc Natl Acad Sci USA, 95:8829-8834 [1998]; Maisonpierre, P. C, et al, Science, 277:55-60 [1997]; Papapetropoulos, A., et al, Lab Invest, 79:213-223 [1999]; Sato, T. N., et al, Nature, 375:70-74 [1998]; Shyu, K. G., et al, Circulation, 95:2081-2087 [1998]; Suri, C, et al, Cell, <37: 1171-1180 [1996]; Suri, C, et al, Science, 252:468-471 [1998]; Valenzuela, D. M., et al, Proceedings of the National Academy of Sciences of the USA, 96:1904-1909 [1999]; Witzenbichler, B., et al, J Biol Chem, 273:18514-18521 [1998]).

Both Ang-1 and -2 bind to Tie-2 with an affinity of 3 nM (Kd) (Maisonpierre, P. C., et al., Science 277 (1997) 55-60). Whereas Ang-1 binding to Tie-2 stimulates receptor phosphorylation in cultured endothelial cells, Ang-2 has been observed to both agonize and antagonize Tie-2 receptor phosphorylation (Davis, S., et al, [1996], supra; Maisonpierre, P. C., et al, [1997], supra; Kim, I, J. H. Kim, et al, Oncogene 19(39): 4549-4552 (2000); Teichert-Kuliszewska, K., P. C. Maisonpierre, et al, Cardiovascular Research 49(3): 659-70 (2001)). The phenotypes of mouse Tie-2 and Ang-1 knockouts are similar and suggest that Ang-1-stimulated Tie-2 phosphorylation mediates remodeling and stabilization of developing vessels in utero through maintenance of endothelial cell-support cell adhesion (Dumont, D. J., et al, Genes & Development, 8:1897-1909 [1994]; Sato, T. N., et al, Nature, 376:10-14 [1995]; Suri, C, et al, [1996], supra). The role of Ang-1 in vessel stabilization is thought to be conserved in the adult, where it is expressed widely and constitutively (Hanahan, D., Science, 277:48-50 [1997]; Zagzag, D., et al, Experimental Neurology, 59:391-400 [1999]). In contrast, Ang-2 expression is primarily limited to sites of vascular remodeling, where it is thought to block Ang-1 function, thereby inducing a state of vascular plasticity conducive to angiogenesis (Hanahan, D., [1997], supra; Holash, J., et al, Science, 284:1994-1998 [1999]; Maisonpierre, P. C, et al, [1997], supra).

Human angiopoietin-2 (Ang-2) (alternatively abbreviated with ANGPT2 or Ang2) is described in Maisonpierre, P. C., et al., Science 277 (1997) 55-60 and Cheung, A. H., et al, Genomics 48 (1998) 389-91. Numerous published studies have purportedly demonstrated vessel-selective Ang-2 expression in disease states associated with deregulated angiogenesis (Bunone, G., et al, American Journal of Pathology, 155:1961-1916 [1999]; Etoh, T., et al, Cancer Research, 67:2145-2153 [2001]; Hangai, M., et al, Investigative Ophthalmology & Visual Science, 42:1611-1625 [2001]; Holash, J., et al, [1999] supra; Kuroda, K., et al, Journal of Investigative Dermatology, 116:113-120 [2001]; Otani, A., et al, Investigative Ophthalmology & Visual Science, 40:1912-1920 [1999]; Stratmann, A., et al, American Journal of Pathology, 153: 1459-1466 [1998]; Tanaka, S., et al, J Clin Invest, 203:34-345 [1999]; Yoshida, Y., et al, International Journal of Oncology, 25:1221-1225 [1999]; Yuan, K., et al, Journal of Periodontal Research, 35:165-171 [2000]; Zagzag, D., et al, [1999] supra). An effective anti-Ang-2 therapy will benefit a vast population of patients with angiogenesis-associated diseases, such as cancer, retinopathies, arthritis, and psoriasis.

There is a great need, therefore, to identify new compounds that specifically recognize and bind Ang-2. Such compounds would be useful for diagnostic screening and therapeutic intervention in disease states that are associated with Ang-2 activity. Accordingly, it is an object of the present disclosure to provide specific binding compounds of Ang-2 for modulating Ang-2 activity. Such compounds disclosed herein take the form of muteins derived from human lipocalin 2 (also known as neutrophil gelatinase associated lipocalin, "hNGAL").

II. DEFINITIONS

The following list defines terms, phrases, and abbreviations used throughout the instant specification. All terms listed and defined herein are intended to encompass all grammatical forms.

As used herein, "Ang-1", unless specified as being from a non-human species (e.g., "mouse Ang-1," "monkey Ang-1," etc.), means human Ang-1, a full-length protein defined by Swiss Prot Q15389 or a biologically active fragment thereof (e.g., a fragment of the Ang-1 protein which is capable of inducing angiogenesis in vitro or in vivo).

As used herein, "Ang-2", unless specified as being from a non-human species (e.g., "mouse Ang-2," "monkey Ang-2," etc.), means human Ang-2, a full-length protein defined by Swiss Prot 015123, (also see, FIG. 6 of U.S. Pat. No. 6,166,185; incorporated herein by reference in its entirety) or a biologically active fragment thereof (e.g., a fragment of the Ang-2 protein which is capable of inducing angiogenesis in vitro or in vivo).

The term "Tie-2" (also referred to in the art as "tek") unless specified as being from a non-human species (e.g., "mouse Tie-2," "monkey Tie-2," etc.), refers to human Tie-2 or a biologically active fragment thereof. Human Tie-2 has the amino acid sequence as set forth in the NCBI protein sequence database under Accession No. AAA61130.

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of human lipocalin 2) to a selected target (in the present case, Ang-1 or Ang-2), can be measured (and thereby KD values of a mutein-ligand complex be determined) by a multitude of methods known to those skilled in the art. Such methods include, but are not limited to, fluorescence titration, direct ELISA, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, direct ELISA, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a compound such as a mutein of the disclosure "specifically binds" a target (for example, Ang-1 or Ang-2) or has "binding specificity" for a target if it is able to discriminate between that target and one or more reference targets, since binding specificity is not an absolute, but a relative property. "Specific binding" can be determined, for example, in accordance with Western blots, ELISA-, RIA-, ECL-, IRMA-tests, IHC and peptide scans.

The term "human lipocalin 2" or "human Lcn 2" or "human NGAL" or "hNGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 16 is used as reference sequence.

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. The term "mutein," as used herein, also includes its functional fragments or variants. Fragments or variants of particular muteins described in the present disclosure preferably retain the function of binding to Ang-1 or Ang-2, e.g. with detectable or even higher affinity, and such fragments or variants are "functional fragments or variants" of the reference mutains disclosed herein.

The term "fragment" as used herein in connection with the muteins of the disclosure relates to proteins or peptides derived from full-length mature human lipocalin 2 that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature human lipocalin 2 and are usually detectable in an immunoassay of the mature human lipocalin 2.

In general, the term "fragment", as used herein with respect to the corresponding protein ligand of a mutein of the disclosure or of the combination according to the disclosure, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature human lipocalin 2 can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the disclosure.

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a mutein different from the wild-type human lipocalin 2 corresponds to a certain position in the amino acid sequence of the wild-type human lipocalin 2, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, the wild-type human lipocalin 2 can serve as "subject sequence" or "reference sequence", while the amino acid sequence of a mutein different from the wild-type human lipocalin 2 described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" human lipocalin 2 is meant human lipocalin 2 that has the same amino acid sequence as the corresponding polypeptide derived from nature. Thus, a native sequence human lipocalin 2 can have the amino acid sequence of the respective naturally-occurring human lipocalin 2. Such native sequence polypeptide can be isolated from nature or can be produced by recombinant or synthetic means. The term "native sequence" polypeptide specifically encompasses naturally-occurring truncated or secreted forms of the human lipocalin 2, naturally-occurring variant forms such as alternatively spliced forms and naturally-occurring allelic variants of human lipocalin 2. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sueqnece positions of one or more muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) human lipocalin 2. Similarly, the position of a given nucleotide in accordance with the present disclosure which may be substituted may vary due to deletions or additional nucleotides elsewhere in a mutein or wild type human lipocalin 2 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a mutein based on a reference scaffold in accordance with the disclosure, it is preferably to be understood that the positions of nucleotides/amino acids are structurally corresponding to the positions elsewhere in a mutein or wild-type human lipocalin 2, even if they may differ in the indicated number.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgous monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

The term "metastasis" according to the disclosure refers to the transmission of cancerous cells from the primary tumor to one or more sites elsewhere in a patient where secondary tumors develop. Means to determine if a cancer has metastasized are known in the art and include bone scan, chest X-ray, CAT scan, MRI scan, and tumor marker tests. The term "prevention of metastasis" means that the metastasis of the primary, tumor or cancer is prevented, delayed, or reduced and thus the development of secondary tumors is is prevented, delayed, or reduced. Preferably the metastasis i.e secondary tumors of the lung are prevented or reduced, which means that metastatic transmission of cancerous cells from the primary tumor to the lung is prevented or reduced.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "vascular diseases" includes Cancer, Inflammatory diseases, Atherosclerosis, lschemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes (such as proliferative retinopathies or age-related macular degeneration (AMD)), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A, Vascular diseases, In: Pathobiology of ocular disease, A dynamic approach, Garner, A., and Klintworth, G. K. (eds.), 2nd edition, Marcel Dekker, New York (1994), pp 1625-1710).

The term "antibody", as used herein, is intended to refer to immunoglobulin molecules comprising four polypeptide chains, two heavy (H) chains and two light (L) chains interconnected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_1$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers.

Alternatively, the antigen-binding fragment of an antibody may contain a monomeric $V_H$ or $V_L$ domain.

III. DESCRIPTIONS OF FIGURES

FIG. 1: demonstrates that lipocalin muteins (SEQ ID NOs: 1, 3, 7, 8, 9, and 11) are capable of blocking the interaction between human Ang-2 and its receptor Tie-2 with an IC50 in a subnanomlar range. Human Ang-2 was pre-incubated with variable concentrations of lipocalin muteins and non-neutralized human Ang-2 was quantified on an ELISA plate with immobilized soluble human Tie-2Fc. Benchmark antibody (SEQ ID NOs: 19/20) was used as positive control. The negative control (SEQ ID NO: 16) has no competitive effect. The data were fitted with a single-site binding model.

Figure 2:
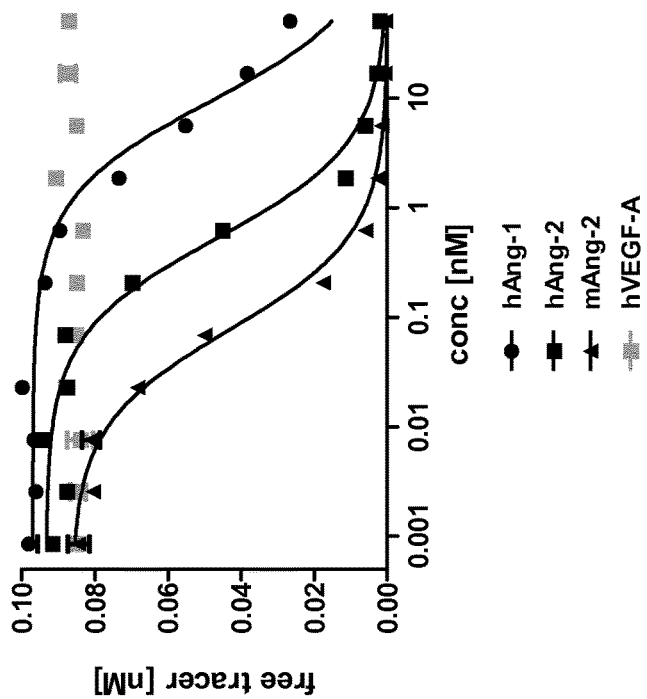
Figure 2:
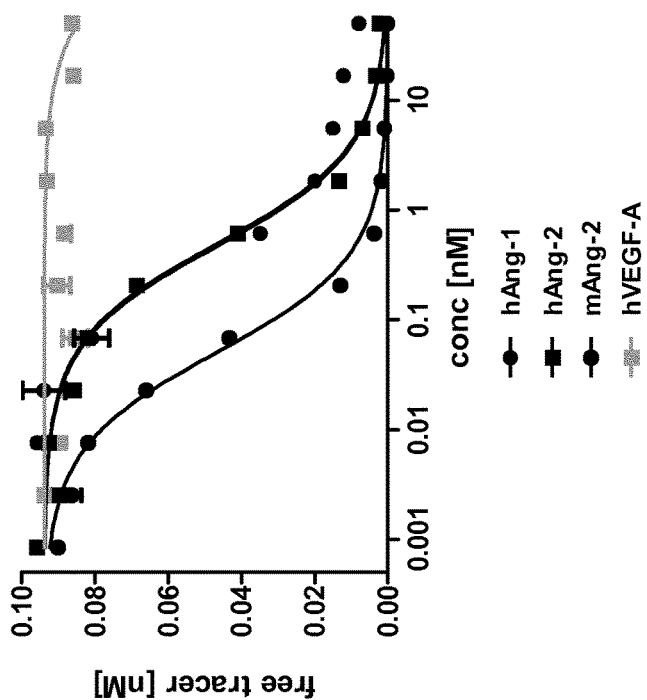

FIG. 2: shows the crossreactivity profile and specificity of lipocalin muteins (SEQ ID NOs: 7 and 8) as measured in a competition ELISA format. The lipocalin muteins are cross-reactive with human Ang-1, human Ang-2 and mouse Ang-2. Data were fitted with a single-site binding model.

Figure 3:
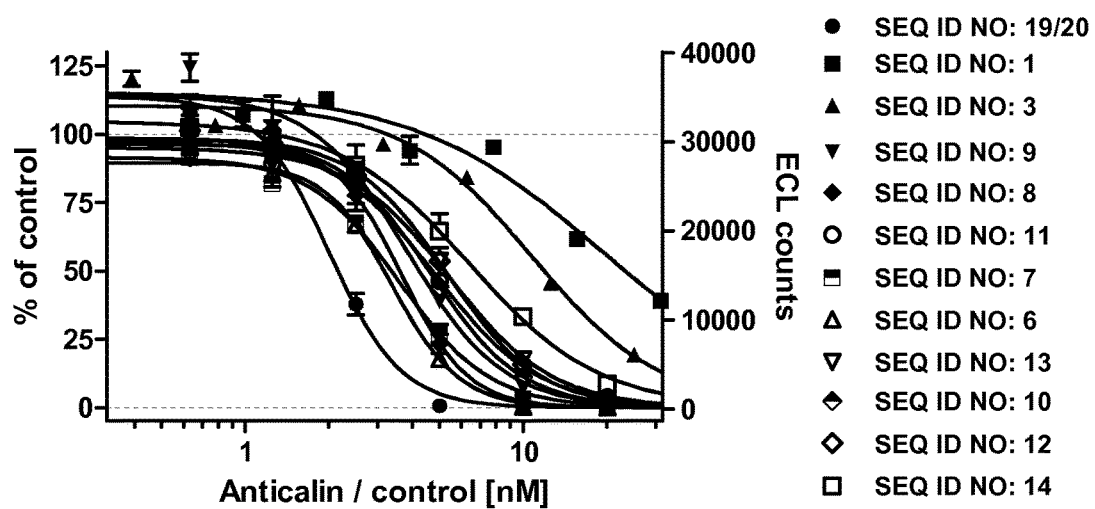

FIG. 3: demonstrates that lipocalin muteins (SEQ ID NOs: 1, 3, 6-14) are capable of blocking the interaction between human Ang-2 and its receptor human Tie-2—over expressed on HEK cell. Human Ang-2 was pre-incubated with variable concentrations of SEQ ID NOs: 1, 3, 6-14 non-neutralized ang-2 was detected via an anti-HIS-tag antibody. Benchmark antibody (SEQ ID NOs: 19/20) was used as positive control. The data were fitted with a single-site binding model.

Figure 4:
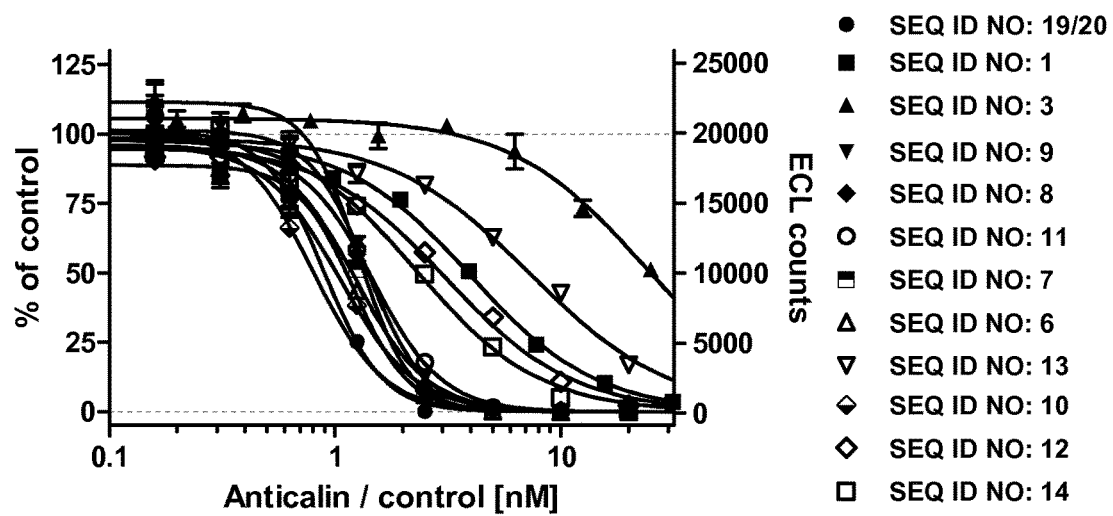

FIG. 4: demonstrates that lipocalin muteins (SEQ ID NOs: 1, 3, 6-14) are capable of blocking the interaction between mouse Ang-2 and the human receptor Tie-2 over expressed on HEK cell. Mouse Ang-2 was pre-incubated with variable concentrations of SEQ ID NOs: 1, 3, 6-14 and non-neutralized mouse Ang-2 was detected via an anti-HIS-tag antibody. Benchmark antibody (SEQ ID NOs: 19/20) was used as positive control. The data were fitted with a single-site binding model.

Figure 5:
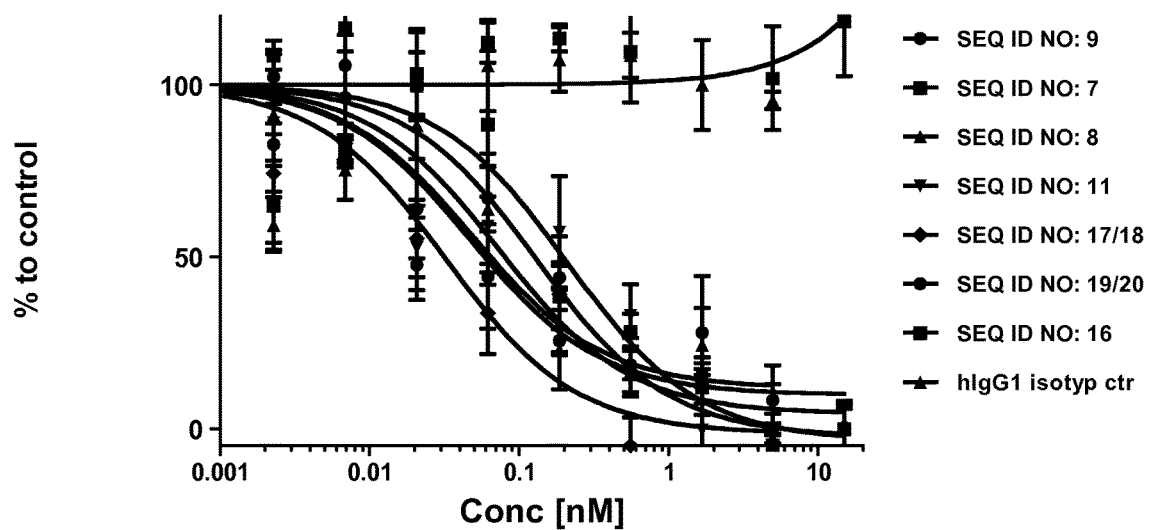

FIG. 5: demonstrates that the lipocalin muteins SEQ ID NOs: 7, 8, 9 and 11 are capable of blocking the biological activity of hAng-2 in a cell-based proliferation assay. In the assay, SEQ ID NOs: 7, 8, 9, 11 and 16, an IgG isotype negative control and two benchmark antibodies were added to starved HLEC. The experiment shows that LEC proliferation is blocked by SEQ ID NOs: 7, 8, 9, 11 and the benchmark antibodies 1 and 2 (benchmark antibody 1: SEQ ID NOs: 17/18; benchmark antibody 2: SEQ ID NOs: 19/20 with similar range IC50 values. The IgG isotype and SEQ ID NO: 16 negative controls had no effect on cell proliferation. Data were fitted with a sigmoidal dose-response model.

IV. DETAILED DESCRIPTION OF THE DISCLOSURE

The current disclosure provides a polypeptide having binding specificity for Ang-2, wherein the polypeptide comprises an hNGAL mutein that binds Ang-2 with detectable affinity.

In some embodiments, an hNGAL mutein binding Ang-2 with detectable affinity may include at least one amino acid substitution of a native cysteine residue by another amino acid, for example, a serine residue. In some other embodiments, a mutein binding Ang-2 with detectable affinity may include one or more non-native cysteine residues substituting one or more amino acids of wild-type hNGAL. In a further particular embodiment, an hNGAL mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Flower, 1996, supra, Flower, et al., 2000, supra) and Breustedt et al. (2005, supra).

A mutein or a composition thereof has specificity for Ang-2 as disclosed herein may have antagonist, or neutralizing or blocking activity with respect to at least one biological activity of Ang-2.

In one aspect, the present disclosure includes various hNGAL muteins that bind Ang-2 with at least detectable affinity. In this sense, Ang-2 is regarded as a non-natural ligand of the reference wild-type hNGAL, where "non-natural ligand" refers to a compound that does not bind to wild-type human lipocalin 2 under physiological conditions. By engineering wild-type hNGAL with one or more mutations at certain sequence positions, the present inventors have demonstrated that high affinity and high specificity for the non-natural ligand, Ang-2, is possible. In some embodiments, at 1, 2, 3, 4, 5, 6, 7, 8, 9, 10, 11, 12 or even more nucleotide triplet(s) encoding certain sequence positions on wild-type I human lipocalin 2, a random mutagenesis may be carried out through substitution at these positions by a subset of nucleotide triplets.

Further, the muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of hNGAL, such as sequence positions 28, 36, 40, 41, 49, 52, 65, 68, 70, 72-74, 77, 79, 81, 87, 96, 100, 103, 106, 116, 125, 126, 127, 129, 132 and 134 of the linear polypeptide sequence of human NGAL (SEQ ID NO: 16).

A mutein of the disclosure may include the wild type (natural) amino acid sequence of the "parental" protein scaffold (such as hNGAL) outside the mutated amino acid sequence positions. In some embodiments, an hNGAL mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human lipocalin 2 as long as these deletions or insertion result in a stable folded/functional mutein (for example, hNGAL muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature hNGAL.

The amino acid sequence of an hNGAL mutein disclosed herein has a high sequence identity to the mature hNGAL (SEQ ID NO: 16) when compared to sequence identities with other lipocalins. In this general context, the amino acid sequence of a mutein of the disclosure is at least substantially similar to the amino acid sequence of the natural wild-type hNGAL, with the proviso that possibly there are gaps (as defined below) in an alignment that are the result of additions or deletions of amino acids. A respective sequence of a mutein of the disclosure, being substantially similar to the sequences of the mature hNGAL, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the mature hNGAL, with the proviso that the altered position or sequence is retained and that one or more gaps are possible.

As used herein, a mutein of the disclosure "specifically binds" a target (for example, Ang-2) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the muteins of the disclosure are fused at its N-terminus and/or its C-terminus to a fusion partner, which, in some particular embodiments, is a protein, or a protein domain or a peptide. In some embodiments, the protein domain may extend the serum half-life of the mutein. In further particular embodiments, the protein domain is an Fc part of an immunoglobulin, a CH3 domain of an immunoglobulin, a CH4 domain of an immunoglobulin, an albumin binding peptide, or an albumin binding protein.

In another embodiment, the muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding peptide, and an albumin binding protein.

In yet another embodiment, the current disclosure relates to a nucleic acid molecule comprising a nucleotide sequence encoding a mutein disclosed herein. The disclosure encompasses a host cell containing said nucleic acid molecule.

A. Exemplary Muteins Specific for Ang-2

In one aspect, the present disclosure relates to novel, specific-binding human lipocalin 2 (human Lcn2 or hNGAL) muteins specific for Ang-2.

One embodiment of the current disclosure relates to a mutein that is capable of binding Ang-2 with detectable affinity, such as an affinity measured by a $K_D$ of about 200 nM or lower, such as about 150 nM or lower.

In one aspect, the current disclosure provides an hNGAL mutein that is capable of binding Ang-2 with a $K_D$ of about 5 nM or lower when measured by Biacore T200 instrument in a Surface Plasmon Resonance (SPR) based assay essentially described in Example 6.

In some further embodiments, one or more hNGAL muteins of this disclsore are capable of binding Ang-2 with an affinity measured by an EC50 value of about 5 nM or lower, when measured in an ELISA assay essentially described in Example 4.

In some other embodiments, one or more hNGAL muteins of this disclsore are capable of binding Ang-2 with an affinity measured by an IC50 value of about 5 nM or lower, when measured in a competition ELISA format assay essentially described in Example 5.

In some other embodiments, one or more hNGAL muteins of this disclsore are capable of inhibiting or reducing lymphatic microvascular endothelial cells proliferation mediated by Ang-2 with an IC50 value of about 5 nM or lower in a cell-based proliferation assay essentially described in Example 9.

In some particular embodiments, an Ang-2-binding hNGAL mutein of the disclosure is capable binding both Ang-2 and Ang-1 with detectable affinity, such as an affinity measured by a $K_D$ of about 200 nM or lower, such as about 150 nM or lower. In some embodiments, one or more hNGAL muteins of this disclsore are crossreactive with both human Ang-1 and human Ang-2.

In some still further embodiments, the mutein is capable of binding Ang-1 with an affinity measured by an IC50 value of about 150 nM or lower, when measured in an ELISA assay essentially described in Example 7.

In some other embodiments, one or more hNGAL muteins of this disclosure are crossreactive with both human Ang-2 and mouse Ang-2. In some embodiments, one ormore such muteins are capable binding both human Ang-2 and mouse Ang-2 with detectable affinity, such as an affinity measured by a $K_D$ of about 200 nM or lower, such as about 150 nM or lower.

In some still further embodiments, one or more such muteins are capable of binding mouse Ang-2 with an affinity measured by an IC50 value of about 5 nM or lower, when measured in an ELISA assay essentially described in Example 7.

In some still further embodiments, one or more such muteins are capable of blocking binding of human Ang-2 to hTie-2 and mouse Ang-2 hTie-2 with an IC50 value of about 25 nM or lower, respectively, in a competition cell ECL format essentially described in Example 8.

In some embodiments, one or more hNGAL muteins of this disclsore are not crossreactive with human Ang-4. In some embodiments, one or more hNGAL muteins of this disclsore are not crossreactive with mouse Ang-3. In some embodiments, one or more hNGAL muteins of this disclsore are not crossreactive with human VEGF-A.

In this regard, the disclosure relates to a polypeptide, wherein said polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40, 41, 49, 52, 65, 68, 70, 72-74, 77, 79, 81, 87, 96, 100, 103, 106, 116, 125, 126, 127, 129, 132 and 134, and wherein said polypeptide binds Ang-2 with detectable affinity.

In some embodiments, an Ang-2-binding hNGAL mutein of the disclosure includes, at any one or more of the sequence positions 36, 40, 41, 49, 52, 68, 70, 72-73, 77, 79, 81, 96, 100, 103, 106, 125, 127, 132 and 134 of the linear polypeptide sequence of the mature hNGAL (SEQ ID NO: 16), one or more of the following mutated amino acid residues: Leu 36→Gln, Glu, His, Val, Met or Phe; Ala 40→Val, Tyr, His or Trp; Ile 41→His, Tyr, Trp or Val; Gln 49→Gly, Ile, Val, Glu or Val; Tyr 52→Trp, His, Thr or Ser; Ser 68→Gly, Asp, Gln, Glu or Ile; Leu 70→Ser, Thr, Gly, Arg, Tyr or Ala; Arg 72→Gly, Ala, Trp, Thr or Glu; Lys 73→Pro, Phe, Leu, Arg, Ala or Gln; Asp 77→Asn, Lys, Ser or Val; Trp 79→Thr, Arg, Ser or Asn; Arg 81→Trp, His or Tyr; Asn 96→Gly, Ala, Pro, Gln or Asp; Tyr 100→Pro, Trp, Gly, Ser, Leu or Asp; Leu 103→Gly, Glu, Aso, Met or Gln; Tyr 106→Thr, Leu or Phe; Lys 125→His, Thr or Gly; Ser 127→Leu or Met; Tyr 132→Phe, Trp or Val; and Lys 134→Ala, Glu or Trp. In some embodiments, an hNGAL mutein of the disclosure includes two or more, such as 3, 4, 5, 6, 7, 8, 9, 10, 11, 12, 13, 14, 15, 16, or even more or all mutated amino acid residues at these sequence positions of the mature hNGAL.

Additionally, an Ang-2-binding hNGAL mutein according to the disclosure may also comprise the following substitution in comparison with the linear polypeptide sequence of the mature hNGAL: Gln 28→His; Asn 65→Asp; Lys 74→Glu; Cys 87→Ser; Asn 116→Asp; Val 126→Met and Asn 129→Asp.

In some additional embodiments, an hNGAL mutein of the disclosure, which binds to Ang-2, includes the following amino acid replacements in comparison with the linear polypeptide sequence of the mature hNGAL:

(a) Gln 28→His; Leu 36→Gln; Ala 40→Tyr; Gln 49→Gly; Tyr 52→Trp; Ser 68→Gly; Leu 70→Ser; Arg 72→Gly; Lys 73→Pro; Asp 77-Asn; Trp 79→Thr; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;

(b) Gln 28→His; Leu 36→Phe; Ala 40→His; Ile 41→Arg; Gln 49→Gly; Tyr 52→His; Ser 68→Asp; Leu 70→Thr; Arg 72→Ala; Lys 73→Phe; Asp 77→Asn; Trp 79→Arg; Arg 81→His; Cys 87→Ser; Tyr 100→Trp; Leu 103→Glu; Tyr 106→Thr; Lys 125→Thr; Ser 127→Met; Tyr 132→Trp; Lys 134→Trp;

(c) Gln 28→His; Leu 36→Val; Ala 40→Trp; Ile 41→Tyr; Gln 49→Ile; Tyr 52→Thr; Ser 68→Gln; Leu 70→Gly; Arg 72→Glu; Lys 73→Gln; Asp 77→Lys; Trp 79→Ser; Arg 81→His; Cys 87→Ser; Tyr 100→Trp; Leu 103→Asp; Tyr 106→Leu; Lys 125→Gly; Ser 127→Met; Tyr 132→Val; Lys 134→Ala;

(d) Gln 28→His; Leu 36→Glu, Ala 40 Nal; Ile 41→Glu; Gln 49→Val; Tyr 52→Thr Ser 68→Glu; Leu 70→Arg; Arg 72→Trp; Lys 73→Leu; Asp 77→Lys; Trp 79→Asn; Arg 81→His; Cys 87→Ser; Asn 96→Ala; Tyr 100→Gly; Leu 103→Met; Tyr 106→Thr; Lys 125→Thr; Ser 127→Met; Tyr 132→Trp; Lys 134→Trp;

(e) Gln 28→His; Leu 36→Gln; Ala 40→Tyr; Ile 41→Trp; Gln 49→Ile; Tyr 52→Ser; Ser 68→Ile; Leu 70→Tyr; Arg 72→Thr; Lys 73→Arg; Asp 77→Ser; Trp 79→Arg; Arg 81→Tyr; Cys 87→Ser; Asn 96→Pro; Leu 103→Asp; Tyr 106→Thr; Lys 125→His; Ser 127→Tyr; Tyr 132→Trp; Lys 134→Glu;

(f) Gln 28→His; Leu 36→Gln; Ala 40→Tyr; Gln 49→Glu; Tyr 52→Trp; Asn 65→Asp; Ser 68→Gly; Leu 70→Ser; Arg 72→Gly; Lys 73→Pro; Asp 77→Asn; Trp 79→Arg; Arg 81→Trp; Cys 87→Ser; Asn 96→Gly; Tyr 100→Ser; Leu 103→Gln; Tyr 106→Thr; Lys 125→His; Ser 127→Leu; Tyr 132→Phe; Lys 134→Glu;

(g) Gln 28→His; Leu 36→His; Ala 40 Tyr; Gln 49→Glu; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Pro; Leu 103→Asp; Tyr 106→Thr; Lys 125→His; Ser 127→Leu; Tyr 132→Phe; Lys 134→Glu;

(h) Gln 28→His; Leu 36→Gln; Ala 40 Tyr; Gln 49→Gly; Tyr 52→Trp; Asn 65→Asp; Ser 68→Glu; Leu 70→Ser; Arg 72→Gly; Lys 73→Ala; Asp 77→Asn; Trp 79→Arg; Arg 81→Trp; Cys 87→Ser; Asn 96→Gly; Tyr 100→Asp; Leu 103→Gly; Tyr 106→Thr; Lys 125→His; Ser 127→Leu; Tyr 132→Phe; Lys 134→Glu;

(i) Gln 28→His; Leu 36→His; Ala 40 Tyr; Gln 49→Gly; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;

(j) Gln 28→His; Leu 36→Gln; Ala 40 Tyr; Gln 49→Gly; Tyr 52→Trp; Asn 65→Asp; Ser 68→Gly; Leu 70→Ser; Arg 72→Gly; Lys 73→Ala; Asp 77→Val; Trp 79→Arg; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;

(k) Gln 28→His; Leu 36→Gln; Ala 40 Tyr; Gln 49→Val; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Leu; Leu 103→Gly; Tyr 106→Thr; Lys 125→His; Ser 127→Leu; Tyr 132→Phe; Lys 134→Glu;

(l) Gln 28→His; Leu 36→Val; Ala 40→Tyr; Ile 41→Tyr; Gln 49→Ile; Tyr 52→Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Cys 87→Ser; Tyr 100→Trp; Leu 103→Asp; Tyr 106→Pro; Asn 116→Asp; Lys 125→Gly; Ser 127→Met; Asn 129→Asp; Tyr 132→Val; Lys 134→Ala;

(m) Gln 28→His; Leu 36→Val; Ala 40→Tyr; Ile 41→Tyr; Gln 49→Ile; Tyr 52→Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Cys 87→Ser; Asn 96→Asp; Tyr 100→Trp; Leu 103→Asp; Tyr 106→Pro; Lys 125→Gly; Val 126→Met; Ser 127→Met; Asn 129→Asp; Tyr 132→Val; Lys 134→Ala; or (n) Gln 28→His; Leu 36→Met; Ala 40→Tyr; Ile 41→Asp; Gln 49→Ile; Tyr 52→Thr; Asn 65→Asp; Ser 68→Gln; Leu 70→Gly; Arg 72→Glu; Lys 73→Gln; Asp 77→Lys; Trp 79→Ser; Arg 81→His; Cys 87→Ser; Asn 96→Gln; Tyr 100→Trp; Leu 103→Asp; Tyr 106→Pro; Lys 125→Gly; Ser 127→Met; Tyr 132→Val; Lys 134→Ala.

In the residual region, i.e. the region differing from sequence positions 28, 36, 40, 41, 49, 52, 65, 68, 70, 72-74, 77, 79, 81, 87, 96, 100, 103, 106, 116, 125, 126, 127, 129, 132 and 134, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 1-14 or a functional fragment or variant thereof. In some embodiments, such fragment or variant is a structural homologue of a mutein defined in any one of SEQ ID NOs: 1-14.

The amino acid sequence of an Ang-2-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 1-14.

In some still embodiments, an hNGAL mutein crossreactive with or binding to human Ang-1, human Ang-2 and/or mouse Ang-2 according to the disclosure comprises an amino acid sequence selected from the group consisting of SEQ ID NOs: 1-14 and functional fragments or variants thereof.

The disclosure also includes structural homologues of an hNGAL mutein having an amino acid sequence selected from the group consisting of SEQ ID NOs: 1-14, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

An Ang-2-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Ang-2, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

The present disclosure also relates to a pharmaceutical composition that includes at least one Ang-2-binding hNGAL mutein disclosed herein, or conjugate or fusion protein thereof as described herein, and optionally, a pharmaceutically acceptable excipient.

Accordingly, the Ang-2-binding hNGAL muteins of the disclosure can be formulated into compositions using pharmaceutically acceptable ingredients as well as established methods of preparation (Gennaro and Gennaro (2000) Remington: *The Science and Practice of Pharmacy*, 20th Ed., Lippincott Williams & Wilkins, Philadelphia, Pa.). To prepare the pharmaceutical compositions, pharmaceutically inert inorganic or organic excipients can be used.

B. Applications of Muteins Specific for Ang-2

Recently, using an ANG-2 knockout mouse model, Yancopoulos' group reported that ANG-2 is required for postnatal angiogenesis (Gale, N. W., et al., Dev. Cell 3 (2002) 411-23). They showed that the developmentally programmed regression of the hyaloid vasculature in the eye does not occur in the ANG-2 knockout mice and their retinal blood vessels fail to sprout out from the central retinal artery (Gale, N. W., et al., Dev. Cell 3 (2002) 411-23). They also found that deletion of ANG-2 results in profound defects in the patterning and function of the lymphatic vasculature (Gale, N. W., et al., Dev. Cell 3 (2002) 411-23). In addition, effective anti-Ang-2 therapy is thought to be of benefit in treating diseases such as cancer, in which progression is dependent on aberrant angiogenesis where blocking the process can lead to prevention of disease advancement (Folkman, J., Nature Medicine. 1, (1995) 27-31). Moreover, Ang-2 expression has been shown to correlate with the severity of various inflammatory and/or infectious diseases (see, e.g., Siner et al., 2009, Shock 31:348-353; Yeo et al., 2008, Proc. Natl. Acad. Sci. (USA): 105: 17097-17102).

Numerous possible applications for the muteins with binding-affinity for Ang-2 of the disclosure, therefore, exist in medicine, for example, in ophthalmology and oncology. In one further aspect, the disclosure relates to the use of such a mutein disclosed herein for detecting Ang-2 in a sample as well as a respective method of diagnosis.

The present disclosure also involves the use of one or more muteins with binding-affinity for Ang-2 as described for complex formation with Ang-2.

Therefore, in another aspect of the disclosure, the disclosed muteins are used for the detection of Ang-2. Such use may include the steps of contacting one or more said muteins, under suitable conditions, with a sample suspected of containing Ang-2, thereby allowing formation of a complex between the muteins and Ang-2, and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The muteins disclosed herein may also be used for the separation of Ang-2. Such use may include the steps of contacting one or more said muteins, under suitable conditions, with a sample supposed to contain Ang-2, thereby allowing formation of a complex between the muteins and Ang-2, and separating the complex from the sample.

In the use of the disclosed muteins for the detection of Ang-2 as well as the separation of Ang-2, the muteins and/or Ang-2 or a domain or fragment thereof may be immobilized on a suitable solid phase.

Accordingly, the presence or absence of a molecule such as Ang-2, e.g., in a sample, as well as its concentration or level may be determined.

The muteins of the present disclosure, therefore, may be used to detect and/or measure Ang-2 in a sample, e.g., for diagnostic purposes. For example, the muteins may be used to diagnose a condition or disease characterized by aberrant expression (e.g., over-expression, under-expression, lack of expression, etc.) of Ang-2. Exemplary diagnostic assays for Ang-2 may comprise, e.g., contacting a sample, obtained from a patient, with the muteins, wherein the muteins are labeled with a detectable label or reporter molecule. Alternatively, unlabeled the muteins can be used in diagnostic applications in combination with a secondary molecule which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase.

Specific exemplary assays that can be used to detect or measure Ang-2 in a sample include enzyme-linked immunosorbent assay (ELISA), radioimmunoassay (RIA), and fluorescence-activated cell sorting (FACS).

In still another aspect, the present disclosure features a diagnostic or analytical kit comprising a mutein with binding-affinity for Ang-2 according to the disclosure.

In a further aspect, the disclosure also encompasses the use of disclosed Ang-2-binding hNGAL muteins or combinations comprising such muteins described herein for the manufacture of a pharmaceutical composition. The pharmaceutical composition thus obtained may be suited for the treatment, prevention and/or amelioration of a disease or disorder associated with deregulated angiogenesis, such as cancer, ocular neovascular diseases (such as retinopathies), arthritis, and psoriasis. The pharmaceutical composition may be used as monotherapy or as combination therapy. Accordingly, the disclosure also provides Ang-2-binding hNGAL muteins for the treatment of a disease or disorder associated with deregulated angiogenesis such as cancer, ocular neovascular diseases (such as retinopathies), arthritis, and psoriasis.

In addition to their use in diagnostics, in yet another aspect, the disclosure encompasses the use of such a mutein of the disclosure or a composition or a combination comprising such mutein for the binding of Ang-2 in a subject and/or inhibiting or reducing angiogenesis in a subject. In some embodiments, such subject may suffer from diseases or disorders associated with deregulated angiogenesis such as cancer, ocular neovascular diseases (such as retinopathies), arthritis, and psoriasis.

In still another aspect, the present disclosure features a method of binding Ang-2 in a subject, comprising administering to said subject an effective amount of one or more muteins with binding-affinity for Ang-2 of the disclosure or of one or more compositions or combinations comprising such a mutein.

In still another aspect, the present disclosure involves a method for inhibiting or reducing angiogenesis in a subject, comprising administering to said subject an effective amount of one or more muteins with binding-affinity for Ang-2 of the disclosure or of one or more compositions or combinations comprising such a mutein. In some embodiments, such subject may suffer from diseases or disorders associated with deregulated angiogenesis such as cancer, ocular neovascular diseases (such as retinopathies), arthritis, and psoriasis.

The muteins of the disclosure or compositions or combinations comprising such muteins are useful, inter alia, for the treatment, prevention and/or amelioration of any disease or disorder associated with Ang-2 activity, including diseases or disorders associated with deregulated angiogenesis.

For example, the muteins or compositions or combinations comprising such muteins of the disclosure may be used to inhibit or reduce tumor growth characterized by undesired angiogenesis in a subject, such as with respect to primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and antigen-binding fragments of the disclosure are used to treat one or more of the following cancers: renal cell carcinoma, pancreatic carcinoma, breast cancer, prostate cancer, malignant gliomas, osteosarcoma, colorectal cancer, malignant mesothelioma, multiple myeloma, ovarian cancer, small cell lung cancer, non-small cell lung cancer, synovial sarcoma, thyroid cancer, or melanoma.

In some other embodiments, the muteins or compositions or combinations comprising such muteins of the present disclosure may also be useful for the treatment, prevention and/or amelioration of one or more eye disorders such as retinopathy. Exemplary eye disorders that can be treated, prevented and/or ameliorated with or by the muteins or compositions comprising such muteins include, e.g., age-related macular degeneration, diabetic retinopathy, and other eye disorders associated with choroidal neovascularization, vascular leak, retinal edema and inflammation. Additionally, the muteins may be administered as an adjuvant to glaucoma surgery to prevent early hem- and lymphangiogenesis and macrophage recruitment to the filtering bleb after glaucoma surgery, and improve clinical outcome.

In some additional embodiments, the muteins or compositions or combinations comprising such muteins are used to treat, prevent or ameliorate vascular diseases such as hypertension, diabetes (including non-insulin dependent diabetes mellitus), psoriasis, arthritis (including rheumatoid arthritis), asthma, sepsis, kidney disease and edema. In some further embodiments, these diseases or disorders are associated with injury, stroke or tumor.

Furthermore, the muteins or compositions or combinations comprising such muteins disclosed herein can be used to treat, prevent or ameliorate one or more inflammatory or infectious diseases. Exemplary infectious diseases that can be treated, prevented or ameliorated by administration of the anti-Ang-2 muteins of the disclosure or compositions comprising such muteins include, but are not limited to, malaria (Plasmodium falciparum infection), viral hemorrhagic fevers (e.g., dengue fever), rickettsial infection, toxic shock syndrome, sepsis, hepatitis C, *Bartonella bacilliformis* infection, *leishmaniasis, mycobacterial* infection, and Epstein-Barr virus infection.

The current disclosure also contemplates the use of the muteins disclosed herein or compositions or combinations comprising such muteins for the preparation of a medicament for the prevention of metastasis or the treatment of cancer or vascular diseases.

The Ang-2-binding hNGAL muteins according to the disclosure or compositions or combinations comprising such muteins can be administered via any parenteral or non-parenteral (e.g. enteral) route that is therapeutically effective. A therapeutically effective route provides for delivery of an agent to a desired compartment, system, or location. For example, a therapeutically effective route is one through which an agent can be administered to provide at the desired site of action an amount of the agent sufficient to effectuate a beneficial or desired clinical result.

C. Combination of Ang-2-Binding mMutein with one or More Anti-Angiogenic Agents

Angiogenesis requires the binding of signaling molecules, such as vascular endothelial growth factor (VEGF), to receptors on the surface of normal endothelial cells. When VEGF and other endothelial growth factors bind to their receptors on endothelial cells, signals within these cells are initiated that promote the growth and survival of new blood vessels. One approach to developing an effective anti-angiogenic treatment modality has been to combine agents that act on different targets involved in angiogenesis, preferably targets that act on well isolated signaling pathways.

The present disclosure, therefore, encompasses the use of an hNGAL mutein of the disclosure specific for Ang-2 in combination with one or more anti-angiogenic agents. As used here, an "anti-angiogenic agent" means any substance is capable of inhibiting or interfering with the binding of one of such signaling molecules to its receptor. In some embodiments, the anti-angiogenic agent is capable of blocking or contributes to block the one of signals that promotes the growth and survival of new blood vessels.

In some particular embodiments, the anti-angiogenic agents comprises (i) antagonists of Ang-1, Ang-2, Ang-3, Ang-4 and/or Tie-2; (ii) antagonists of Fltl, KDR, Flt4, VEGF-A, VEGF-B, VEGF-C, VEGF-D, VEGF-E, PlGF and/or EG-VEGF; (iii) delta like ligand 4 (DLL4, a vascular-specific Notch ligand) antagonists, (iv) epidermal growth factor receptor (EGFR) antagonists and (v) cytokine inhibitors.

In some still further embodiments, the Ang-2 antagonist may be an hNGAL mutein of the disclosure, an anti-Ang-2 antibody (see U.S. Pat. No. 8,133,979; incorporated herein by reference in its entirety), peptibody (see U.S. Pat. No. 8,129,331; incorporated herein by reference in its entirety), or CovX-body (such as CVX-060, see U.S. Pat. No. 7,521,425; incorporated herein by reference in its entirety). In some further embodiments, the DLL4 antagonist may be an anti-DLL4 antibody (e.g., an anti-DLL4 antibody disclosed in U.S. Patent Application No. 2009/0142354 such as REGN421 and etc.). In some further embodiments, the EGFR antagonist may be an anti-EGFR antibody or small molecule inhibitor of EGFR activity. Other anti-angiogenic agents that may be beneficially administered in combination with the anti-Ang-2 hNGAL muteins of the disclosure include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, and/or to their respective receptors.

In this regard, the present disclosure also includes therapeutic combinations comprising any of the anti-Ang-2 hNGAL muteins mentioned herein and an anti-angiogenic agent such as an antagonist of one or more of VEGF, DLL4, EGFR, or any of the aforementioned cytokines, wherein the antagonist may be an aptamer, an antisense molecule, a ribozyme, an siRNA, a peptibody, a nanobody, an antibody, an antibody fragment (e.g., Fab fragment; F(ab')$_2$ fragment; Fd fragment; Fv fragment; scFv; dAb fragment; an engineered molecule (such as diabody, triabody, tetrabody, minibody and minimal recognition unit); an antiviral, an antibiotic, an analgesic, a corticosteroids and/or an nonsteroidal anti-inflammatory drug (NSAID).

In some embodiments, said engineered molecule may be an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, a "kappabody" (Ill. et al. "Design and construction of a hybrid immunoglobulin domain with properties of both heavy and light chain variable regions" Protein Eng 10:949-57 (1997)), a "minibody" (Martin et al. "The affinity-selection of a minibody polypeptide inhibitor of human interleukin-6" EMBO J 13:5303-9 (1994)), a "diabody" (Holliger et al. "Diabodies': small bivalent and bispecific antibody fragments" PNAS USA 90:6444-6448 (1993)), a "janusin" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, or an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat Biotech. 2005 Nov. 20 edition).

When combined with one or more additional agents of the disclosure, the anti-Ang-2 hNGAL muteins may be administered prior to, simultaneous with (e.g., in the same formulation or in separate formulations), or subsequent to the administration of the other agent(s). The hNGAL mutein and the anti-angiogenic agent may be administered in combination, including concurrently, concomitantly or in series. In some embodiments, the combinations of the disclosure, the hNGAL muteins and the anti-angiogenic agents, may be included in a single composition that may be administered. The composition may include an effective amount of the hNGAL mutein and the anti-angiogenic agent as active ingredients, in association with at least one pharmaceutically acceptable adjuvant, diluent or carrier. In this regard, the combinations of the disclosure can be formulated into compositions using pharmaceutically acceptable ingredients as well as established methods of preparation (Gennaro and Gennaro (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used.

The hNGAL mutein and the anti-angiogenic agent may also be administered independent from each other, including at individual intervals at independent points of time. The combinations of the hNGAL mutein and the anti-angiogenic agent may be provided in various forms and in any orientation.

The anti-Ang-2 hNGAL muteins of the disclosure and combinations thereof may also be administered as part of a treatment regimen that also includes radiation treatment and/or conventional chemotherapy.

In some particular embodiments, the anti-angiogenic agent is an antagonist of any component of the VEGF/VEGF receptor systems and Angiopoietin/Tie-2 receptor system; that is any one of Fltl, KDR, Flt4, VEGF-A, VEGF-B, VEGF-C, VEGF-D, VEGF-E, PlGF, EG-VEGF, Ang-1, Ang-2, Ang-3, Ang-4 or Tie-2. The VEGF-VEGFR pathway and the Tie-2 pathway should be considered as two independent mediators essential for the process of in vivo angiogenesis (Siemeister, G., et al., Cancer Res. 59:3 (1999) 3185-91; Jendreyko, N., et al., Journal of Biological Chemistry, 278:47812-47819 (2003); Jendreyko, N., et al., PNAS, 102:8293-8298 (2005)).

In some still further embodiments, the anti-angiogenic agent is a VEGF inhibitor. The VEGF family includes VEGF-A, VEGF-B, VEGF-C, VEGF-D, VEGF-E, placental growth factor (PlGF) and endocrine gland-derived VEGF (EG-VEGF). Members of the VEGF family are known to bind with different affinities to three related receptor tyrosine kinases; VEGFR1 (the fms-like tyrosine kinase receptor, Fltl), VEGFR2 (the kinase insert domain-containing receptor, KDR), and VEGFR3 (another fms-like tyrosine kinase receptor, Flt4).

A "VEGF inhibitor" as used herein means any substance that decreases signaling by the VEGF-VEGFR pathway. Therefore, VEGF inhibitor may inhibit or interfere with any member of the VEGF family and/or any one of the receptor tyrosine kinases. VEGF inhibitors can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signaling pathway. Still other VEGF inhibitors act by altering regulatory posttranslational modifications that modulate VEGF-VEGFR pathway signaling. VEGF inhibitors in accordance with the disclosure also may act through more indirect mechanisms. Whatever the mechanism involved, as used herein, a VEGF inhibitor decreases the effective activity of the VEGF-VEGFR signaling pathway in a given circumstance over what it would be in the same circumstance in the absence of the inhibitor.

In some particular embodiments, the VEGF inhibitor may be a VEGF-Trap (see, e.g., U.S. Pat. No. 7,087,411; incorporated herein by reference in its entirety), an anti-VEGF antibody (e.g., bevacizumab), a small molecule kinase inhibitor of VEGF receptor (e.g., sunitinib, sorafenib or pazopanib), an anti-VEGF tear lipocalin mutein (see, e.g. PCT application PCT/EP2007/057971, incorporated herein by reference in its entirety) or anti-VEGFR tear lipocalin mutein (see, e.g. PCT application PCT/EP2007/057971, incorporated herein by reference in its entirety).

In some embodiments, the VEGF inhibitor, as the anti-angiogenic agent, is selected from the group consisting of VEGF-Trap (see, e.g., U.S. Pat. No. 7,087,411; incorporated herein by reference in its entirety), bevacizumab (Avastin®), sorafenib (Nexavar®), sunitinib (Sutent®) and pazopanib (Votrient®).

In some additional embodiments, the VEGF inhibitor may be an antagonist of VEGF-A, such as an anti-VEGF-A antibody (e.g., bevacizumab). In some other embodiments, the VEGF-A antagonist may be a lipocalin mutein that has binding specificity for VEGF-A (see, e.g. PCT application PCT/EP2007/057971; incorporated herein by reference in its entirety).

In some additional embodiments, the VEGF inhibitor may be an antagonist of VEGF-C, such as an anti-VEGF-C antibody (see, e.g., U.S. Pat. Nos. 6,403,088 and 8,486,397; incorporated herein by reference in their entirety). In some other embodiments, the VEGF-C antagonist may be a lipocalin mutein that has binding specificity for VEGF-C.

In some embodiments, an hNGAL mutein of the disclosure specific for Ang-2 in combination with more than one anti-angiogenic agents, such as two, wherein one agent is a VEGF-A antagonist mentioned herein and the second agent is a VEGF-C antagonist mentioned herein.

In some embodiments, the present disclosure encompasses the use of (i) an hNGAL mutein of the disclosure specific for Ang-2 and (ii) one or more anti-angiogenic agents, for inhibiting deregulated angiogenesis in a subject. Such use includes a step of administering to a subject an effective amount of (i) an hNGAL mutein of the disclosure specific for Ang-2 and (ii) one or more anti-angiogenic agents.

Similarly, the present disclosure discloses the use of (i) an hNGAL mutein of the disclosure specific for Ang-2 and (ii) one or more anti-angiogenic agents for the treatment, prevention or alleviation of diseases or disorders associated with deregulated angiogenesis in a subject. In some further embodiments, the diseases or disorders associated with deregulated angiogenesis include cancer, ocular neovascular diseases (such as retinopathies), arthritis, and psoriasis. In some embodiments, one anti-angiogenic agent is a VEGF-A antagonist mentioned herein and the second anti-angiogenic agent is a VEGF-C antagonist mentioned herein.

Further details on hNGAL muteins with a detectable affinity for Ang-2 can be found in Section A of the current disclosure.

In a particularly preferred embodiment, an hNGAL mutein that is specific for Ang-2 is selected from the group consisting of SEQ ID NOs: 1-14 and functional fragments or variants thereof. In some embodiments, such fragments or variants are structural homologues of a mutein defined in any one of SEQ ID NOs: 1-14.

The present disclosure also relates to a pharmaceutical composition comprising at least one of the following: (i) an hNGAL mutein of the disclosure specific for Ang-2 and (ii) one or more anti-angiogenic agents, which composition can be used in for inhibiting deregulated angiogenesis. In some embodiments, one anti-angiogenic agent is a VEGF-A antagonist mentioned herein and the second anti-angiogenic agent is a VEGF-C antagonist mentioned herein.

In this regard, the combinations of the disclosure can be formulated into compositions using pharmaceutically acceptable ingredients as well as established methods of preparation (Gennaro and Gennaro (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used.

In still another aspect, the present disclosure features a method of treating, preventing or ameliorating diseases or disorders associated with deregulated angiogenesis in a subject, comprising administering to said subject an effective amount of a composition that comprises at least the following: (i) a mutein of hNGAL that has a detectable affinity to Ang-2 and (ii) one or more anti-angiogenic agents. In some further embodiments, the diseases or disorders associated with deregulated angiogenesis include cancer, ocular neovascular diseases (such as retinopathies), arthritis, and psoriasis. In some embodiments, one anti-angiogenic agent is a VEGF-A antagonist mentioned herein and the second anti-angiogenic agent is a VEGF-C antagonist mentioned herein.

In still another aspect, the present disclosure involves a method of inhibiting or reducing deregulated angiogenesis in a subject comprising administering to said subject an effective amount of a composition that comprises at least the following: (i) a mutein of hNGAL that has a detectable affinity to Ang-2 and (ii) one or more anti-angiogenic agents. In some embodiments, one anti-angiogenic agent is a VEGF-A antagonist mentioned herein and the second anti-angiogenic agent is a VEGF-C antagonist mentioned herein.

D. Muteins of the Disclosure

When used herein in the context of the muteins of the present disclosure that bind to Ang-2, the term "specific for" includes that the mutein is directed against, binds to, or reacts with Ang-2. Thus, being directed to, binding to or reacting with includes that the mutein specifically binds to Ang-2. The term "specifically" in this context means that the mutein reacts with an Ang-2, as described herein, but essentially not with another target. Whether the mutein specifically reacts as defined herein above can easily be tested, inter alia, by comparing the reaction of a hNGAL mutein of the present disclosure with Ang-2 and the reaction of said mutein with (an) other target(s). "Specific binding"

can also be determined, for example, in accordance with Western blots, ELISA-, RIA-, ECL-, IRMA-tests, FACS, IHC and peptide scans.

The amino acid sequence of a mutein according to the disclosure has a high sequence identity to human lipocalin 2 when compared to sequence identities with another lipocalin (see also above). In this general context the amino acid sequence of a mutein of the combination according to the disclosure is at least substantially similar to the amino acid sequence of the corresponding lipocalin (the wild-type hNGAL). A respective sequence of a mutein of the combination according to the disclosure, being substantially similar to the sequence of mature hNGAL, such as at at least 65%, at least 70%, at least 75%, at least 80%, at least 82%, at least 85%, at least 87%, at least 90% identity, including at least 95% identity to the sequence of mature hNGAL. In this regard, a mutein of the disclosure of course may contain, in comparison substitutions as described herein which renders the mutein capable of binding to Ang-2. Typically a mutein of hNGAL includes one or more mutations relative to the native sequence of hNGAL of amino acids in the four loops at the open end of the ligand binding site of hNGAL. As explained above, these regions are essential in determining the binding specificity of a mutein for Ang-2. A mutein derived hNGAL or a homologue thereof, may have one, two, three, four or more mutated amino acid residues at any sequence position in the N-terminal region and/or in the three peptide loops BC, DE, and FG arranged at the end of the β-barrel structure that is located opposite to the natural binding pocket.

A mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native hNGAL alin, provided that such a mutein should be capable of binding to Ang-2. For example, a mutein can have a substitution at a position corresponding to a distinct position (i.e. at a corresponding position) of hNGAL. In some embodiments a mutein of the combination according to the disclosure includes at least two amino acid substitutions, including 2, 3, 4, 5, or even more, amino acid substitutions of a native amino acid by an arginine residue. Accordingly, the nucleic acid of a protein 'reference' scaffold as described herein is subject to mutagenesis with the aim of generating a mutein which is capable of binding to Ang-2.

Also, a mutein of the present disclosure can comprise a heterologous amino acid sequence at its N- or C-Terminus, preferably C-terminus, such as a Strep-tag, e.g., Strep II tag without affecting the biological activity (binding to its target e.g. Ang-2) of the mutein.

Specifically, in order to determine whether an amino acid residue of the amino acid sequence of a mutein different from wild-type hNGAL corresponds to a certain position in the amino acid sequence of wild-type hNGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, wild-type hNGAL can serve as "subject sequence" or "reference sequence", while the amino acid sequence of a mutein different from the wild-type hNGAL described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the mutein retains its capability to bind Ang-2, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

a. Alanine (Ala), Glycine (Gly);
b. Aspartic acid (Asp), Glutamic acid (Glu);
c. Asparagine (Asn), Glutamine (Gin);
d. Arginine (Arg), Lysine (Lys);
e. Isoleucine (Ile), Leucine (Leu), Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of hNGAL are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of hNGAL also may be substituted, generally with serine, to improve the oxidative stability of the molecule and prevent aberrant crosslinking. Conversely, cysteine bond (s) may be added to improve its stability.

Any mutation, including an insertion as discussed above, can be accomplished very easily on the nucleic acid, e.g.

DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Modifications of the amino acid sequence include directed mutagenesis of single amino acid positions in order to simplify sub-cloning of the mutated hNGAL gene or its parts by incorporating cleavage sites for certain restriction enzymes. In addition, these mutations can also be incorporated to further improve the affinity of a mutein for a given target such as Ang-2. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a mutein of the disclosure, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue.

With respect to a mutein of human lipocalin 2, exemplary possibilities of such a mutation to introduce a cysteine residue into the amino acid sequence of a lipocalin including human lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of human NGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No. P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In another embodiment, in order to provide suitable amino acid side chains for conjugating one of the above compounds to a mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

In some embodiments, a mutein of the disclosure may be fused at its N-terminus or its C-terminus to a protein, a protein domain or a peptide, for instance, a signal sequence and/or an affinity tag.

Affinity tags such as the Strep-Tag® or Strep-Tag® II(Schmidt, T. G. M. et al. (1996) *J. Mol. Biol.* 255, 753-766), the myc-tag, the FLAG-tag, the His$_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for muteins of the disclosure as well.

In general, it is possible to label the muteins of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the disclosure. The muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The muteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a mutein of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a mutein with binding activity for albumin. Accordingly, suitable conjugation partners for extending the half-life of a mutein of the disclosure include an albumin binding protein, for example, a bacterial albumin binding domain, such as the one of streptococcal protein G (König, T., & Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in U.S. Patent Application 2003/0069395 (incorporated herein by reference in its entirety) or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a mutein of the disclosure. The term "albumin" includes all mammal albumins such as human serum albumin or bovine serum albumin or rat albumine. The albumin or fragment thereof can be recombinantly produced as described in U.S. Pat. No. 5,728,553 or European Patent Applications EP 0 330 451 and EP 0 361 991 (incorporated herein by reference in their entirety). Recombinant human albumin (Recombumin®) Novozymes Delta Ltd. (Nottingham, UK) can be conjugated or fused to a mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and Mass., USA).

Using transferrin as a moiety to extend the serum half-life of the muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, Pa., USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the disclosure, the SynFusion™ technology, commercially available from Syntonix Pharmaceuticals, Inc (Mass., USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. Nos. 6,500,930 or 6,620,413, carbohydrate oligo- and polymers such as starch or hydroxyethyl starch (HES) can be conjugated to a mutein of the disclosure for the purpose of serum half-life extension.

In addition, a mutein disclosed herein may be fused to a moiety may confer new characteristics to the muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a mutein disclosed herein with a separate enzyme active site such that both "components" of the resulting fusion protein together act on a given therapeutic target. The binding domain of the mutein attaches to the disease-causing target, allowing the enzyme domain to abolish the biological function of the target.

The present disclosure also relates to nucleic acid molecules (DNA and RNA) that include nucleotide sequences encoding the muteins of the disclosure. Since the degeneracy of the genetic code permits substitutions of certain codons by other codons specifying the same amino acid, the disclosure is not limited to a specific nucleic acid molecule encoding a mutein as described herein but encompasses all nucleic acid molecules that include nucleotide sequences encoding a functional mutein. In this regard, the present disclosure provides nucleotide sequences, as shown in SEQ ID NOs: 21-34, encoding some muteins of the disclosure.

In one embodiment of the disclosure, the method includes subjecting the nucleic acid molecule to mutagenesis at nucleotide triplets coding for at least one, or even more, of the sequence positions corresponding to the sequence positions 28, 36, 40, 41, 49, 52, 65, 68, 70, 72-74, 77, 79, 81, 87, 96, 100, 103, 106, 116, 125, 126, 127, 129, 132 and 134 of the linear polypeptide sequence of human NGAL (SEQ ID NO: 16).

The disclosure also includes nucleic acid molecules encoding the muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae, Pichia pastoris*, SF9 or High5 insect cells, immortalized mammalian cell lines (e.g., HeLa cells or CHO cells) or primary mammalian cells.

The disclosure also relates to a method for the production of a mutein as described herein, wherein the mutein or polypeptide, a fragment of the mutein or a fusion protein of the mutein is produced starting from the nucleic acid coding for the mutein or polypeptide by means of genetic engineering methods. The method can be carried out in vivo, the mutein or polypeptide can for example be produced in a bacterial or eucaryotic host organism and then isolated from this host organism or its culture. It is also possible to produce a protein in vitro, for example by use of an in vitro translation system.

When producing the mutein in vivo a nucleic acid encoding such mutein or polypeptide is introduced into a suitable bacterial or eukaryotic host organism by means of recombinant DNA technology (as already outlined above). For this purpose, the host cell is first transformed with a cloning vector that includes a nucleic acid molecule encoding a mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in hNGAL muteins of the disclosure. Accordingly, such muteins can be produced in a cell compartment having a reducing redox milieu, for example, in the cytoplasma of Gram-negative bacteria.

In case a mutein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the disclosure in the cytosol of a host cell, preferably *E. coli*. In this case, the mutein or polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, the mutein or polypeptide as described herein may not necessarily be generated or produced only by use of genetic engineering. Rather, such mutein or polypeptide can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for Ang-2. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the mutein or polypeptide of the disclosure may be produced by in vitro transcription/translation employing well-established methods known to those skilled in the art.

The skilled worker will appreciate methods useful to prepare muteins or polypeptides thereof contemplated by the present disclosure but whose protein or nucleic acid sequences are not explicity disclosed herein. As an overview, such modifications of the amino acid sequence include, e.g., directed mutagenesis of single amino acid positions in order to simplify sub-cloning of a mutated hNGAL gene or its parts by incorporating cleavage sites for certain restriction enzymes. In addition, these mutations can also be incorporated to further improve the affinity of a mutein for its target (e.g. Ang-2 or Ang-1, respectively). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The muteins or polypeptides thereof disclosed herein and their derivatives can be used in many fields similar to antibodies or fragments thereof. For example, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, muteins or polypeptides thereof of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1

Selection of Muteins Specifically Binding to Ang-2

Libraries, generated by random mutagenesis of mature hNGAL, were used for selection of muteins specifically binding to the human Ang-2.

$2 \times 10^{12}$ phagemids from these libraries were incubated with 200 nM biotinylated human Ang-2 (R & D System). Paramagnetic beads coated with neutravidin or streptavidin were used to capture target/phagemid complexes which were subsequently isolated with a magnet. Unbound phagemids were removed by washing the beads with PBST or PBS. Bound phagemids were first eluted with 300 μl 70 mM triethylamine followed by immediate neutralization of the supernatant with 100 μl 1M Tris-Cl pH 6.0. After one intermediate wash cycle remaining phagemids were eluted with 100 mM glycin pH 2.2 for 10 min followed by immediate neutralization with 50 μl 0.5 M Tris-base. Both elution fractions were pooled and used to infect 4 ml of *E. coli* XL1-blue culture for reamplification.

Four consecutive rounds of selection were performed. Phagemid DNA was prepared from *E. coli* cells infected with the output of the fourth selection round and an hNGAL mutein cassette was isolated by digestion. The hNGAL mutein cassette was inserted into the likewise cut vector, which allows bacterial production of the hNGAL muteins under the control of a tetracyclin promoter. CaCl2-competent TG1-F' cells were transformed with the ligation mixture and plated on LB/Amp plates.

For optimization of Ang-2 specific muteins, additional libraries were generated based on mutein SEQ ID NO: 1 and SEQ ID NO: 3. Libraries were generated using either a biased randomization of selected positions or error prone polymerase chain reaction (PCR) based methods. Selection of optimized muteins was performed as described above but with increased stringency.

Example 2

Identification of Muteins Specifically Binding to Ang-2 Using High-Throughput ELISA Screening Individual colonies were used to inoculate 2×YT/Amp medium and grown overnight (14-18 h) to stationary phase. Subsequently, 50 μl 2×YT/Amp were inoculated from the stationary phase cultures and incubated for 3 h at 37° C. and then shifted to 22° C. until an $OD_{595}$ of 0.6-0.8 was reached. Production of muteins was induced by addition of 10 μl 2×YT/Amp supplemented with 1.2 μg/ml anhydrotetracyclin. Cultures were incubated at 22° C. until the next day. After addition of 40 μl of 5% (w/v) BSA in PBS/T and incubation for 1 h at 25° C. cultures were ready for use in screening assays.

Specific binding of the isolated muteins to human Ang-2 was tested by coating a 1:1 mixture of neutravidin and streptavidin (5 μg/ml in PBS) overnight at 4° C. on microtiterplates. After blocking the plate 1 h with 2% BSA in PBST the biotinylated target used for selection was captured on the coated microtiterplates at a concentration of 1 μg/ml in PBS/T. Plates coated in the same manner without biotinylated target were used as negative control target in the screening. Subsequently, 20 µl of BSA-blocked cultures were added to the coated microtiter plate containing either captured target or aldosterone and incubated for 1 h at 25° C. Bound muteins were detected after 1 h incubation with an anti-Streptag antibody conjugated with horseradish peroxidase (IBA, Boettingen). For quantification, 20 µl of QuantaBlu fluorogenic peroxidase substrate was added and the fluorescence determined at an excitation wavelength of 320 nm and an emission wavelength of 430 nm. Muteins specifically binding to Ang-2 were then sequenced.

To select for muteins with increased affinity and stability, screening was performed with i) reduced antigen concentration and/or ii) competiton with Tie-2 Fc (Reliatech) and/or iii) incubation of the screening supernatant at 65° C. or 70° C. before addition to the target plate and/or iv) using reverse screening formats were the muteins were captured via the Streptag on microtiter plates coated with anti-Streptag antibody (Qiagen) and different concentrations of target was added and detected via HRP-labelled anti-His-tag antibody (Abcam).

Example 3

Expression of Muteins

Unique muteins were expressed with C-terminal sequence (SEQ ID NO: 15) including the Strep-Tag® II, in 2YT-Amp media to purify the muteins after expression using Strep-Tactin affinity chromatography and preparative size exclusion chromatography were applicable.

Example 4

Affinity of Muteins to Ang-2 in an ELISA Based Setting

Binding of muteins was tested by a sandwich ELISA assay. In detail, a 384-well plate suitable for fluorescence measurements (Greiner FLUOTRACT™ 600, black flat bottom, high-binding) was coated with 20 µl of Ang-2 at a concentration of 5 µg/ml in PBS over night at 4 C. After washing, the Ang-2-coated wells were blocked with 100 µl blocking buffer containing 0.1% Tween 20 and 2% BSA (PBS-T/BSA) for 1 h at room temperature.

20 µl of serially diluted muteins were incubated in PBS-T/BSA for 1 h at room temperature (RT).

The residual supernatants were discarded and 20 µl HRP-labeled anti-Streptag antibody was added at a predetermined optimal concentration in PBS-T/BSA and incubated for 1 h at RT. After washing, 20 µl fluorogenic HRP substrate (QuantaBlu, Thermo) was added to each well, and the reaction was allowed to proceed for 15 to 60 minutes. The fluorescence intensity of every well on the plate was read using a fluorescence microplate reader (Tecan or Molecular Devices). Curve fitting was performed using GraphPad Prism 4 software. The resulting EC50 values are summarized in Table 1 below.

TABLE 1

| Mutein SEQ ID | EC50 mean [nM] |
| --- | --- |
| SEQ ID NO: 1 | 3.7 |
| SEQ ID NO: 2 | 3 |

TABLE 1-continued

| Mutein SEQ ID | EC50 mean [nM] |
| --- | --- |
| SEQ ID NO: 3 | 2.8 |
| SEQ ID NO: 5 | 3.5 |
| SEQ ID NO: 7 | 2.1 |
| SEQ ID NO: 8 | 2.4 |
| SEQ ID NO: 9 | 2.1 |
| SEQ ID NO: 11 | 2.3 |

Example 5

Competitive Mode of Action of Lipocalin Mutein Binding to Ang-2

Whether the selected muteins bind to human Ang-2 in a competitive mode was tested in vitro using a competition ELISA format assay (see exemplary lipocalin muteins in FIG. 1). In this experiment, a constant concentration of human Ang-2 was incubated with variable concentrations of lipocalin muteins for 1 h. After this pre-incubation in solution, an aliquot of the lipocalin mutein/Ang-2 mixture was transferred to an ELISA plate coated with human Tie-2 receptor to measure the concentration of hAng-2 that was not blocked to bind to hTie-2.

All incubation steps were performed with shaking at 300 rpm, and the plate was washed after each incubation step with 80 µl PBS-T buffer (PBS, 0.05% Tween 20) for five times using a Biotek EL405 select CW washer (Biotek). In the first step, a 384 well plate was directly coated with 20 µl of soluble human hTie-2 Fc (Reliatech) at a concentration of 2 µg/ml in PBS over night at 4° C. After washing, h Tie-2 Fc coated wells were blocked with 60 µl PBS-T/BSA (2% BSA in PBS containing 0.1% Tween 20) for 1 h at room temperature.

A fixed concentration of 0.5 nM human Ang-2 was incubated in solution with varying concentrations of SEQ ID NOs: 1-14, or with SEQ ID NO: 16 as a negative control and with benchmark antibodies 1 and 2 (SEQ ID NOs: 17/18 and 19/20, respectively) as a positive controls, using a suitable starting concentration which was serially diluted at a 1:3 ratio down to the picomolar range in PBS-T/BSA buffer. After 1 h incubation at room temperature, 20 µl of the reaction mixture was transferred to the hTie-2 Fc-coated plate to capture unbound (free) or non-competitively bound hAng-2 for 20 min at RT. To allow for transformation of ELISA readout results into absolute free Ang-2 concentrations (cf. below), a standard curve containing varying concentrations of hAng-2 was prepared in PBS-T/BSA and incubated for 20 min on the same plate as well.

To allow for detection and quantitation of bound hAng-2, the residual supernatants were discarded and 20 µl anti-HIS-tag HRP-labeled antibody was added at a concentration in PBS-T/BSA and incubated for 1 h at RT. After washing, 20 µl quanta blue was added to each well and the fluorescence intensity of every well was read using a fluorescence microplate reader (Tecan or Molecular Devices).

The evaluation was performed as follows: free hAng-2 concentration $c(Ang-2)_{free}$ was calculated (from the standard curve determined in parallel) and plotted versus SEQ ID NOs: 1-14, 16, and benchmark antibodies 1 and 2 (SEQ ID NOs: 17/18 and 19/20, respectively) concentration, c(SEQ ID NOs: 1-14, 16, 17/18 and 19/20). To obtain the SEQ ID NOs: 1-14, 16, 17/18 and 19/20 concentration at which formation of the hAng-2/hTie-2 Fc-complex was blocked by 50% (IC50), the curves were fitted by nonlinear regression with a single-sites binding model according to $c(Ang-2)_{free} = c(Ang-2)_{tot}/(1+c(SEQ\ ID\ NOs:\ 1-14,\ 16,\ 17/18\ and\ 19/20)/1050))$, with the total tracer concentration $c(Ang-2)_{tot}$ and the IC50 value as free parameters (as shown in FIG. 1). Curve fitting was performed using GraphPad Prism 4 software. The resulting IC50 values are summarized in Table 2 below.

TABLE 2

| Mutein SEQ ID | IC50 mean [nM] |
|---|---|
| SEQ ID NO: 1 | 0.5581 |
| SEQ ID NO: 2 | 1.711 |
| SEQ ID NO: 3 | 0.3194 |
| SEQ ID NO: 4 | 0.4123 |
| SEQ ID NO: 5 | 0.8613 |
| SEQ ID NO: 6 | 0.06273 |
| SEQ ID NO: 7 | 0.06193 |
| SEQ ID NO: 8 | 0.07083 |
| SEQ ID NO: 9 | 0.09287 |
| SEQ ID NO: 10 | 0.07940 |
| SEQ ID NO: 11 | 0.09877 |
| SEQ ID NO: 12 | 0.1312 |
| SEQ ID NO: 13 | 0.1842 |
| SEQ ID NO: 14 | 0.1054 |
| SEQ ID NO: 19/20 | 0.03067 |
| SEQ ID NO: 17/18 | 0.01580 |

Example 6

Affinity of Muteins Binding to Ang-2 Determined in Biacore

In a Surface Plasmon Resonance (SPR) based assay, a Biacore T200 instrument (GE Healthcare) was used to measure the binding affinity of muteins to hAng-2. Muteins selected for binding to Ang-2 and negative control (SEQ ID NO: 16) were biotinylated for 2 h at room temperature applying an appropriate excess of EZ-Link NHS-PEG4-Biotin (Thermo). Biotinylated samples were purified from non-reacted Biotin using a Zeba Spin Desalting Plate (Thermo) according to the manufactures instructions.

In the SPR affinity assay, biotinylated muteins and negative control were captured on a sensor chip CAP using the Biotin CAPture Kit (GE Healthcare): Sensor Chip CAP is pre-immobilized with an ssDNA oligo. Undiluted Biotin CAPture Reagent (streptavidin conjugated with the complementary ss-DNA oligo) was applied at a flow rate of 2 µl/min for 300 s. Subsequently, 0.02 µg/mL of biotinylated muteins or negative control were applied for 300 s at a flow rate of 5 µl/min. As the analyte Ang-2 is a multimeric molecule, it was aimed to create a surface with minimal ligand density to reduce bivalent interactions on the chip surface to a minimum. The reference channel was loaded with Biotin CAPture Reagent only.

To determine the binding affinity, four dilutions of human Ang-2 at concentrations in the range of 1-27 nM were prepared in HBS-EP+ buffer (GE Healthcare) and applied to the prepared chip surface. Applying a flow rate of 30 µL/min, a multi cycle kinetics approach was used with a sample contact time of 180 s and a dissociation time of 4600 s. All measurements were performed at 25° C. Regeneration of the Sensor Chip CAP surface was achieved with an injection of 6 M Gua-HCl with 0.25 M NaOH followed by an extra wash with running buffer or water and a stabilization period of 120 s. Data were evaluated with Biacore T200 Evaluation software (V 1.0). Double referencing was used. A 1:1 Binding model was used to fit the raw data even though the analyte was known to be a multimer.

The resulting kinetic constants for a selection of lipocalin muteins are summarized in Table 3 below. Such exemplary lipocalin muteins (SEQ ID NOs: 7, 8, 9 and 11) bind human Ang-2 with affinities in the range of 0.2-1.4 nM while no binding is detectable for the negative control (SEQ ID NO: 16). It has to be noted, that the fitted values were derived based on the assumption that using a very low ligand density with Rmax values below ten reduces multivalent interactions to a negligible level.

TABLE 3

| Mutein SEQ ID | $k_{on}$ [M$^{-1}$ * s$^{1}$] | $k_{off}$ [s$^{-1}$] | KD [nM] | Rmax [RU] |
|---|---|---|---|---|
| SEQ ID NO: 9 | 3.2E+05 | 9.4E−05 | 0.29 | 5.4 |
| SEQ ID NO: 7 | 1.8E+05 | 2.6E−04 | 1.43 | 8.1 |
| SEQ ID NO: 8 | 3.5E+05 | 1.3E−04 | 0.37 | 6.5 |
| SEQ ID NO: 11 | 4.0E+06 | 8.7E−04 | 0.21 | 2.6 |

Example 7

Specificity and Species Crossreactivity of Lipocalin Mutein to Ang-1 and Ang-2

Specificity and species crossreactivity of the lipocalin muteins (SEQ ID NOs: 1, 3, 7, 8, 9, 11) and of the benchmark antibody (SEQ ID NOs: 17/18) were tested by a "solution competition ELISA" assay (see exemplary lipocalin muteins FIG. 2), the principle of which was as follows: A constant concentration of SEQ ID NOs: 1, 3, 7, 8, 9, 11 and benchmark antibody (SEQ ID NOs: 17/18) was incubated with variable concentrations of ligands (human Ang-2, human Ang-1, human Ang-4, mouse Ang2 and mouse Ang 3 as well as hVEGF-A as negative control (R&D system)) or 1 h. After this pre-incubation in solution, an aliquot of the mutein/ligand mixture was transferred to an ELISA plate with hAng-2 immobilized to measure the remaining concentration of free lipocalin muteins SEQ ID NOs: 1, 3, 7, 8, 9, 11, and of free benchmark antibody. The concentration of free (unbound) SEQ ID NOs: 1, 3, 7, 8, 9, 11, and of free benchmark antibody was determined via a quantitative ELISA setup. Note that this assay relied on that all ligands were targeting the same binding site on SEQ ID NOs: 1, 3, 7, 8, 9, 11, and 17/18, i.e. that the ligands bound to the SEQ ID NOs: 1, 3, 7, 8, 9, 11, and 17/18 in competition with each other.

In the following detailed experimental protocol, incubation and washing steps were performed as described above in the competition ELISA protocol (see Example 5). A 384-well plate suitable for fluorescence measurements (Greiner FLUOTRACT™ 600, black flat bottom, high-binding) was coated with 20 µl of h Angiopoietin 2 of 5 µg/ml in PBS over night at 4° C. After washing, the Ang-2-coated wells were blocked with 100 µl blocking buffer (PBS-T/BSA) for 1 h at room temperature.

A fixed concentration of 0.1 nM of SEQ ID NOs: 1, 3, 7, 8, 9, 11, and 17/18 were incubated in solution with varying concentrations of ligands (hAng-2, mAng-2, hAn1, mAng-3 and hAng-4 and VEGF-A), using a suitable starting concentration which was serially diluted at a 1:3 ratio down to the picomolar range in PBS-T/BSA. After 1 h incubation at room temperature, 20 µl of the reaction mixture was transferred to the 384-well plate upon which hAng-2 was immobilized to capture unbound (free SEQ ID NOs: 1, 3, 7, 8, 9, 11, and 17/18 for 20 min at RT. To allow for transformation of ELISA readout results into absolute free SEQ ID NOs: 1, 3, 7, 8, 9, 11, and 17/18 concentrations (cf. below), a standard curve containing varying concentrations SEQ ID NOs: 1, 3, 7, 8, 9, 11, and 17/18 were prepared in PBS-T/BSA and incubated for 20 min on the same ELISA plate as well.

The residual supernatants were discarded and 20 µl HRP-labeled anti-lipocalin-mutein antibody was added at a pre-determined optimal concentration in PBS-T/BSA and incubated for 1 h at RT. The anti-lipocalin-mutein antibody had been obtained by immunization of rabbits with a mixture of lipocalin muteins, and was subsequently coupled to HRP using a kit (EZ-link Plus Activated Peroxidase, Thermo Scientific) according to the manufacturer's intructions, to obtain the antibody-HRP conjugate. After washing, 20 µl fluorogenic HRP substrate (Quantablue, Pierce) was added to each well, and the reaction was allowed to proceed for 60 minutes. The fluorescence intensity of every well on the plate was read using a Genios Plus Microplate reader (Tecan). To evaluate the data, free muteins concentration, c(Mutein)$_{free}$, was calculated based on the standard curve results, and plotted versus ligand concentration, c(Ligand). To obtain the ligand concentration at which formation of the hAng-2/Mutein complex was blocked by 50% (IC50), the curves were fitted by nonlinear regression with a single-sites binding model according to c(Mutein)$_{free}$=c(Mutein)$_{tot}$/(1+ c(Ligand)/IC50)), with the total tracer concentration c(Mutein)$_{tot}$ and the IC50 value as free parameters. Curve fitting was performed using GraphPad Prism 4 software. Said curve fitting yielded the results that are summarized in the following Table 4.

this pre-incubation in solution, an aliquot of the lipocalin mutein/Ang-2 mixture was transferred to an MSD plate coated with hTie-2 overexpressing HEK cells to measure the concentration of hAng-2 or mAng-2 that was not blocked to bind to hTie-2 respectively.

All incubation steps were performed at room temperature, and the plate was washed after each incubation step with 80 µl PBS buffer for two times using a Biotek EL405 select CW washer (Biotek). In the first step, a 384 well plate was precoated for 5 minutes with poly D lysine and washed twice with PBS. $10^4$ HEK:hTie-2 cells per well were seeded and allowed to adhere to the surface of the wells overnight at 37° C. After washing, cell coated wells were blocked with 60 µl PBS/Casein (2% Casein in PBS) for 1 h at room temperature.

A fixed concentration of human Ang-2 or of mouse Ang-2 was incubated in solution with varying concentrations of SEQ ID NOs: 1, 3, 6-14 and of benchmark antibody (SEQ ID NO: 19/20) using a suitable starting concentration of SEQ ID NOs: 1, 3, 6-14 and of benchmark antibody which was serially diluted at a 1:3 ratio down to the picomolar range in PBS-/Casein buffer. After 1 h incubation at room temperature, 20 µl of the reaction mixture was transferred to the HEK:hTie2-coated plate to capture competitively unbound hAng-2 for 1 hour min at RT. A standard curve containing varying concentrations of hAng-2 or mouse Ang-2 was prepared in PBS/Casein and incubated for 1 hour the same plate as well.

To allow for detection and quantitation of bound hAng-2 and mouse Ang-2, the residual supernatants were discarded and 20 µl of a mixture anti-HIS-tag antibody (Abcam) and Sulfotag labelled anti-goat antibody (Mesoscale Discovery) was added at a concentration of 1 µg/ml in PBS/casein and

TABLE 4

| | Solution binding ELISA IC50: nM | | | | | |
|---|---|---|---|---|---|---|
| | hAng-1 | hAng-2 | mAng-2 | hAng-4 | mAng-3 | hVEGF-A |
| SEQ ID NO: 17/18 | 26 | 0.6 | 0.07 | N/A | N/A | N/A |
| SEQ ID NO: 3 | N/A | 1.4 | 1.8 | N/A | N/A | N/A |
| SEQ ID NO: 1 | >100 | 2.5 | 0.65 | N/A | N/A | N/A |
| SEQ ID NO: 11 | 0.89 | 0.49 | 0.05 | N/A | N/A | N/A |
| SEQ ID NO: 8 | 9.3 | 0.5 | 0.08 | N/A | N/A | N/A |
| SEQ ID NO: 7 | 0.47 | 0.41 | 0.05 | N/A | N/A | N/A |
| SEQ ID NO: 9 | 1.9 | 0.76 | 0.11 | N/A | N/A | N/A |

As depicted in FIG. 2, the data demonstrates that SEQ ID NO: 8 displayed high affinity towards human and mouse Ang-2 and SEQ ID NO: 7 displayed high affinity not only towards human and mouse Ang-2 but also towards human Ang-1.

Example 8

Lipocalin Muteins Blocking the Binding of Human and Mouse Ang-2 to hTie-2 Expressing Cells Whether lipocalin muteins binds to human Ang-2 and mouse Ang-2 in a competitive mode was tested on hTie-2 overexpressing HEK cells using a competition cell electrochemoluminescence (ECL) assay format (see FIGS. 3 and 4). In this experiment, a constant concentration of human Ang-2 and mouse Ang-2 was incubated with variable concentrations of lipocalin muteins (SEQ ID NOs: 1, 3, 6-14) and benchmark antibody (SEQ ID NOs: 19/20) for 1 h. After incubated for 1 h at RT. After washing, 35 µl surfactant-free reading buffer was added to each well and the ECL signal of every well was read using a Mesoscale Discovery reader.

Evaluation and curve fitting was performed using Graph Pad Prism 4 software and the yielded results are summarized in Table 5 below.

TABLE 5

| mutein SEQ ID | hAng2 IC50 [nM] | mAng-2 IC50 [nM] |
|---|---|---|
| SEQ ID NO: 3 | 10.73 | 23.17 |
| SEQ ID NO: 1 | 18.91 | 3.982 |
| SEQ ID NO: 6 | 3.464 | 1.206 |
| SEQ ID NO: 7 | 3.596 | 1.228 |
| SEQ ID NO: 8 | 3.746 | 1.245 |
| SEQ ID NO: 9 | 3.817 | 1.39 |
| SEQ ID NO: 10 | 4.626 | 1.046 |
| SEQ ID NO: 11 | 4.793 | 1.448 |
| SEQ ID NO: 12 | 5.287 | 3.118 |

TABLE 5-continued

| mutein SEQ ID | hAng2 IC50 [nM] | mAng-2 IC50 [nM] |
|---|---|---|
| SEQ ID NO: 13 | 5.431 | 7.343 |
| SEQ ID NO: 14 | 6.41 | 2.32 |
| SEQ ID NO: 19/20 | 1.999 | 0.8826 |

Example 9

Lipocalin-Mutein-Mediated Blockade of Ang-2 in Cell-Based Proliferation Assay

The ability of the lipocalin muteins of SEQ ID NOs: 1, 3, 7-9 and 11 to neutralize the biological acitivity of hAng-2 was assessed by the application of a short-term proliferation bioassay employing lymphatic microvascular endothelial cells (LEC). The LEC proliferation can be inhibited by agents having hAng-2-neutralizing effect. In the assay, SEQ ID NOs: 1, 3, 7-9 and 11 were added to serum starved LEC cells in culture. After three days in culture, the extent of proliferation was assessed by quantifying the number of viable cells. This was performed using the CellTiter-Glo Luminescent Cell Viability Assay (Promega) to measure ATP levels, which correlate with the number of metabolically active cells. The ability of SEQ ID NOs: 1, 3, 7-9 and 11 to neutralize hAng-2 was assessed by their IC50 value, i.e. the concentration of the lipocalin muteins that lead to half-maximal inhibition of hAng-2 mediated proliferation.

The detailed procedure of setting up the assay is hereby described in the following. LEC were maintained in EBM, 5% fetal calf serum and MV2 supplemental kit. Assays were performed in 96 wells white clear flat-bottom plates (Greiner) in 25 µL per well.

LEC cells were cultured in cell culture flasks under standard conditions according to manufacturer's instuction (PAA Laboratories), 37° C., 5% CO$_2$ atmosphere).

On day 1 of the experiment, the adherent cells were dissociated from their substrate with trypsin/EDTA according to the manufacturer's instructions. Subsequently, cells were centrifuged down for 5 minutes at 1000 rpm, resuspended in EBM and filtered through a 100 µm cell strainer (Falcon) to remove cell aggregates. Cells were then seeded in 96-well flat bottom tissue culture plates (Greiner) at a density of 3200 cells per well using an end volume of 100 µl. They were incubated 1 hour under standard conditions.

After 1 h dilution series of SEQ ID NOs: 1, 3, 7-9, 11, of negative controls (SEQ ID NO: 16 and a human IgG isotype antibody (Dianova)) and of benchmark antibodies 1 and 2 (SEQ ID NOs: 17/18 and 19/20, respectively) were added to the wells. All titration series were performed with a serial 1:3 dilution in assay medium and a suitable starting concentration. Subsequently, the cells were allowed to proliferate for 72 hours at 37° C. To quantify cell proliferation after 72 hours, 25 µL CellTiter-Glo reagents were added to the cells in each of the wells and incubated for 2 minutes on an orbital shaker to induce cell lysis, and luminescence was measured using the PheraStar FS reader.

IC50 values were determined using GraphPad Prism software (GraphPad Software Inc.) by plotting standardized signal agains samples' concentration and non-linear regression of the data with a sigmoidal dose-response model.

The result of the experiment is shown in FIG. 5. The proliferation assay disclosed above is representative of three independent experiments. The results are summarized in Table 6 below.

TABLE 6

| Mutein SEQ ID | IC50 mean [nM] |
|---|---|
| SEQ ID NO: 1 | 2.252 |
| SEQ ID NO: 3 | 2.806 |
| SEQ ID NO: 7 | 0.1992 |
| SEQ ID NO: 8 | 0.0780 |
| SEQ ID NO: 9 | 0.1423 |
| SEQ ID NO: 11 | 0.1692 |
| SEQ ID NO: 17/18 | 0.0668 |
| SEQ ID NO: 19/20 | 0.0435 |

SEQ ID NO: 8 displayed an average EC50 of 0.07 nM, benchmark antibody 1 (SEQ ID NOs: 17/18) exhibited an EC50 of 0.06 nM, and benchmark antibody 2 (SEQ ID NOs: 19/20) exhibited an EC50 of 0.04 nM. The negative controls had no effect on proliferation. The data therefore demonstrates that SEQ ID NO: 8 and the benchmark antibodies exhibit a comparable potency in this functional assay.

Example 10

Stability Assessment of Muteins

The resulting melting temperatures (Tm) as well as the onset of melting for the lipocalin muteins (SEQ ID NOs: 1, 3, 7-9, 11) are listed in Table 7 below in comparision with benchmark antibody (SEQ ID NOs: 17/18). The lipocalin muteins selected have Tm ranging from 65 to 77° C., indicating good stability of the molecules.

TABLE 7

Tm and onset of melting as determined by nanoDSC of Ang-2 specific lipocalin muteins and benchmark antibody

| Mutein SEQ ID | Tm [° C.] | onset of melting [° C.] |
|---|---|---|
| SEQ ID NO: 1 | 64 | 59 |
| SEQ ID NO: 3 | 66 | 59 |
| SEQ ID NO: 7 | 76 | 68 |
| SEQ ID NO: 8 | 73 | 63 |
| SEQ ID NO: 9 | 77 | 70 |
| SEQ ID NO: 11 | 75 | 65 |
| SEQ ID NO: 17/18 | 69.5/76.1/83.4 | 64 |

To assess storage stability, exemplary muteins at a conc. of 1 mg/ml in PBS were incubated for 1 week at 37° C. Active mutein was measured in a quantitative ELISA setting. Monomeric protein was measured in an analytical size exclusion chromatography. Resulted data for SEQ ID NOs: 1, 3, 7-9 and 11 are shown in Table 8 below.

To test protein activity, the following ELISA was applied: A 384-well plate suitable for fluorescence measurements (Greiner FLUOTRAC™ 600, black flat bottom, high-binding) was coated with 20 µL of Ang-2 (Thermo Scientific) at a concentration of 5 µg/ml in PBS overnight at 4° C. After washing, the Ang-2-coated wells were blocked with 100 µl blocking buffer (2% w/v BSA in PBS containing 0.1% v/v Tween-20) for 1 h. The plate was washed and 20 μl of appropriately diluted protein standard, unstressed reference sample or stressed sample was transferred to the ELISA plate and incubated. To quantitate plate-bound protein, the ELISA plate was washed, residual supernatants were discarded and 20 μl HRP-labeled anti-hNGAL antibody was added at a predetermined optimal concentration in blocking buffer and incubated. After washing, 20 μl fluorogenic HRP substrate (QuantaBlu, Pierce) was added to each well, and the reaction was allowed to proceed for 20-30 minutes. The fluorescence intensity of every well on the plate was read using a fluorescence microplate reader (Tecan).

Unless otherwise stated all incubation steps were performed at for 1 h at room temperature and after each incubation step the plate was washed with 100 μl PBS-T buffer (PBS, 0.05% Tween 20) for five times using a Biotek ELx405 select CW washer.

For the ELISA described above, a calibration curve including 11 dilutions typically ranging from 0.008-500 ng/mL was prepared and three different, independent dilutions within the linear range of the calibration curve were prepared for each sample. Blocking buffer optionally supplemented with 1% human or murine plasma was used for the dilutions.

The calibration curve was fit using a 4 Parameter Logistic (4PL) nonlinear regression model and used to calculate active protein concentrations for the tested samples. The determined active protein concentrations were referenced against an unstressed sample stored at the same concentration and in the same matrix.

Analytical size exclusion chromatography was performed on an Agilent HPLC system with two Superdex 75 5/150 GL columns (GE Healthcare) in a row using PBS (Gibco) as an eluent at a flow rate of 0.3 mL/min.

To assess storage stability in plasma, exemplary muteins at a conc. of 0.5 mg/ml were incubated for 1 week at 37° C. in human and mouse plasma. Active mutein was measured in a quantitative ELISA setting as described above.

All tested lipocalin muteins proved to be stable under all tested conditions and the test results are summarized in Table 8 below.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

TABLE 8

Stability after 3 freeze/thaw cycles (F/T); 1 week storage in PBS at 37° C. and 1 week storage in human (hu) or mouse (mu) plasma assessed by recovery of activity in qELISA and monomer content in analytical SEC: stable in qELISA = 100 +/− 15%; stable in aSEC = 100 +/− 5% (recovery of monomer peak area compared to non-stressed reference sample); for all samples including references a monomer content of 100 area percent has been detected.

| Mutein SEQ ID | Freeze/thaw | | 1 week PBS 37° C. | | 1 week hu plasma | 1 week mu Plasma |
| --- | --- | --- | --- | --- | --- | --- |
| | Q ElISA | HPLC | Q ElISA | HPLC | Q ElISA | Q ElISA |
| SEQ ID NO: 2 | 104 | 100 | 94 | 97 | — | — |
| SEQ ID NO: 3 | 95 | 98 | 100 | 96 | — | — |
| SEQ ID NO: 1 | 102 | 103 | 99 | 105 | — | — |
| SEQ ID NO: 7 | — | — | — | — | 99 | 85 |
| SEQ ID NO: 8 | — | — | — | — | 89 | 93 |
| SEQ ID NO: 9 | — | — | — | — | 99 | 100 |
| SEQ ID NO: 11 | — | — | — | — | 100 | 89 |
| SEQ ID NO: 17/18 | 108 | 109 | 87 | 103 | — | — |

The invention claimed is:

1. A human neutrophil gelatinase associated lipocalin (hNGAL) mutein that is capable of binding angiopoietin-2 (Ang-2) with detectable affinity,
wherein the mutein comprises the following mutated amino acid residue in comparison with the linear polypeptide sequence of mature hNGAL (SEQ ID NO: 16): Gln 28→His,
wherein the mutein comprises at least fifteen of the following mutated amino acid residues in comparison with the linear polypeptide sequence of mature hNGAL (SEQ ID NO: 16): Leu 36→Gln, Glu, His, Val, Met or Phe; Ala 40→Val, Tyr, His or Trp; Ile 41→His, Tyr, Trp, Val, Arg, Glu, or Asp; Gln 49→Gly, Ile, Glu or Val; Tyr 52→Trp, His, Thr or Ser; Ser 68→Gly, Asp, Gln, Glu or Ile; Leu 70→Ser, Thr, Gly, Arg, Tyr or Ala; Arg 72 Gly, Ala, Trp, Thr or Glu; Lys 73→Pro, Phe, Leu, Arg, Ala or Gln; Asp 77→Asn, Lys, Ser or Val; Trp 79→Thr, Arg, Ser or Asn; Arg 81→Trp, His or Tyr; Asn 96→Gly, Ala, Pro, Gln or Asp; Tyr 100→Pro, Trp, Gly, Ser, Leu or Asp; Leu 103→Gly, Glu, Asp, Met or Gln; Tyr 106→Thr, Leu, Phe, or Pro; Lys 125→His, Thr or Gly; Ser 127→Leu, Met, or Tyr; Tyr 132→Phe, Trp or Val; and Lys 134→Ala, Glu or Trp, and
wherein the mutein has a sequence identity of at least 85% to a sequence selected from the group consisting of SEQ ID NOs: 1-14.

2. The hNGAL mutein of claim 1, wherein the mutein is capable of binding Ang-2 with a dissociation constant (KD) of about 5 nM or lower.

3. The hNGAL mutein of claim 1, wherein the mutein is capable of binding Ang-2 with an affinity measured by an EC50 value of about 5 nM or lower.

4. The hNGAL mutein of claim 1, wherein the mutein is capable of binding Ang-2 with an affinity measured by an IC50 value of about 5 nM or lower.

5. The hNGAL mutein of claim 1, wherein the mutein is capable of inhibiting or reducing lymphatic microvascular endothelial cell proliferation mediated by Ang-2 with an IC50 value of about 5 nM or lower.

6. The hNGAL mutein of claim 1, wherein the mutein comprises a mutated amino acid residue at sixteen or more positions corresponding to positions 36, 40, 41, 49, 52, 65, 68, 70, 72-74, 77, 79, 81, 87, 96, 100, 103, 106, 116, 125, 126, 127, 129, 132, and 134 of the linear polypeptide sequence of mature hNGAL (SEQ ID NO: 16).

7. The hNGAL mutein of claim 1, wherein the mutein comprises one or more of the following mutated amino acid residues in comparison with the linear polypeptide sequence of mature hNGAL (SEQ ID NO: 16): Asn 65→Asp; Lys 74→Glu; Cys 87→Ser; Asn 116→Asp; Val 126→Met; and Asn 129→Asp.

8. The hNGAL mutein of claim 1, wherein the mutein comprises one of the following sets of mutated amino acid residues in comparison with the linear polypeptide sequence of mature hNGAL (SEQ ID NO: 16):
(a) Gln 28→His; Leu 36→Gln; Ala 40→Tyr; Gln 49→Gly; Tyr 52→Trp; Ser 68→Gly; Leu 70→Ser; Arg 72→Gly; Lys 73→Pro; Asp 77→Asn; Trp 79→Thr; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;
(b) Gln 28→His; Leu 36→Phe; Ala 40→His; Ile 41→Arg; Gln 49→Gly; Tyr 52→His; Ser 68→Asp; Leu 70→Thr; Arg 72→Ala; Lys 73→Phe; Asp 77→Asn; Trp 79→Arg; Arg 81→His; Cys 87→Ser; Tyr 100→Trp; Leu 103→Glu; Tyr 106→Thr; Lys 125→Thr; Ser 127→Met; Tyr 132→Trp; Lys 134→Trp;
(c) Gln 28→His; Leu 36→Val; Ala 40→Trp; Ile 41→Tyr; Gln 49→Ile; Tyr 52→Thr; Ser 68→Gln; Leu 70→Gly; Arg 72→Glu; Lys 73→Gln; Asp 77→Lys; Trp 79→Ser; Arg 81→His; Cys 87→Ser; Asn 96→Asp; Tyr 100→Trp; Leu 103→Asp; Tyr 106→Leu; Lys 125→Gly; Ser 127→Met; Tyr 132→Val; Lys 134→Ala;
(d) Gln 28→His; Leu 36→Glu, Ala 40→Val; Ile 41→Glu; Gln 49→Val; Tyr 52→Thr Ser 68→Glu; Leu 70→Arg; Arg 72→Trp; Lys 73→Leu; Asp 77→Lys; Trp 79→Asn; Arg 81→His; Cys 87→Ser; Asn 96→Ala; Tyr 100→Gly; Leu 103→Met; Tyr 106→Thr; Lys 125→Thr; Ser 127→Met; Tyr 132→Trp; Lys 134→Trp;
(e) Gln 28→His; Leu 36→Gln; Ala 40→Tyr; Ile 41→Trp; Gln 49→Ile; Tyr 52→Ser; Ser 68→Ile; Leu 70→Tyr; Arg 72→Thr; Lys 73→Arg; Asp 77→Ser; Trp 79→Arg; Arg 81→Tyr; Cys 87→Ser; Asn 96→Pro; Leu 103→Asp; Tyr 106→Thr; Lys 125→His; Ser 127→Tyr; Tyr 132→Trp; Lys 134→Glu;
(f) Gln 28→His; Leu 36→Gln; Ala 40→Tyr; Gln 49→Glu; Tyr 52→Trp; Asn 65→Asp; Ser 68→Gly; Leu 70→Ser; Arg 72→Gly; Lys 73→Pro; Asp 77→Asn; Trp 79→Arg; Arg 81→Trp; Cys 87→Ser; Asn 96→Gly; Tyr 100→Ser; Leu 103→Gln; Tyr 106→Thr; Lys 125→His; Ser 127→Leu; Tyr 132→Phe; Lys 134→Glu;
(g) Gln 28→His; Leu 36→His; Ala 40→Tyr; Gln 49→Glu; Tyr 52→Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Pro; Leu 103→Asp; Tyr 106→Thr; Lys 125→His; Ser 127→Leu; Tyr 132→Phe; Lys 134→Glu;
(h) Gln 28→His; Leu 36→Gln; Ala 40→Tyr; Gln 49→Gly; Tyr 52 Trp; Asn 65→Asp; Ser 68→Glu; Leu 70→Ser; Arg 72→Gly; Lys 73→Ala; Asp 77→Asn; Trp 79→Arg; Arg 81→Trp; Cys 87→Ser; Asn 96→Gly; Tyr 100→Asp; Leu 103→Gly; Tyr 106→Thr; Lys 125→His; Ser 127→Leu; Tyr 132→Phe; Lys 134→Glu;
(i) Gln 28→His; Leu 36→His; Ala 40→Tyr; Gln 49→Gly; Tyr 52 Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;
(j) Gln 28→His; Leu 36→Gln; Ala 40→Tyr; Tyr 52 Trp; Asn 65→Asp; Ser 68→Gly; Leu 70→Ser; Arg 72→Gly; Lys 73→Ala; Asp 77→Val; Trp 79→Arg; Arg 81→Trp; Cys 87→Ser; Asn 96→Gly; Tyr 100→Pro; Leu 103→Gly; Tyr 106→Thr; Lys 125→His; Ser 127→Leu; Tyr 132→Phe; Lys 134→Glu;
(k) Gln 28→His; Leu 36→Gln; Ala 40→Tyr; Gln 49→Val; Tyr 52 Trp; Asn 65→Asp; Ser 68→Glu; Leu 70→Ser; Arg 72→Gly; Lys 73→Pro; Asp 77→Asn; Trp 79→Arg; Arg 81→Trp; Cys 87→Ser; Asn 96→Gly; Tyr 100→Leu; Leu 103→Gly; Tyr 106→Thr; Lys 125→His; Ser 127→Leu; Tyr 132→Phe; Lys 134→Glu;
(l) Gln 28→His; Leu 36→Val; Ala 40→Trp; Ile 41→Tyr; Gln 49→Ile; Tyr 52 Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Cys 87→Ser; Tyr 100→Trp; Leu 103→Asp; Tyr 106→Pro; Asn 116→Asp; Lys 125→Gly; Ser 127→Met; Asn 129→Asp; Tyr 132→Val; Lys 134→Ala;
(m) Gln 28→His; Leu 36→Val; Ala 40→Trp; Ile 41→Tyr; Gln 49→Ile; Tyr 52 Thr; Asn 65→Asp; Ser 68→Gln; Leu 70→Gly; Arg 72→Glu; Lys 73→Gln; Lys 74→Glu; Asp 77→Lys; Trp 79→Ser; Arg 81→His; Cys 87→Ser; Asn 96→Asp; Tyr 100→Trp; Leu 103→Asp; Tyr 106→Pro; Lys 125→Gly; Val 126→Met; Ser 127→Met; Asn 129→Asp; Tyr 132→Val; Lys 134→Ala; or
(n) Gln 28→His; Leu 36→Met; Ala 40→Trp; Ile 41→Asp; Gln 49→Ile; Tyr 52 Thr; Asn 65→Asp; Ser 68→Gln; Leu 70→Ala; Arg 72→Glu; Lys 73→Gln; Asp 77→Lys; Trp 79→Ser; Arg 81→His; Cys 87→Ser; Asn 96→Gln; Tyr 100→Trp; Leu 103→Asp; Tyr 106→Pro; Lys 125→Gly; Ser 127→Met; Tyr 132→Val; Lys 134→Ala.

9. The hNGAL mutein of claim 1, wherein the mutein comprises an amino acid sequence selected from the group consisting of SEQ ID NOs: 1-14.

10. The hNGAL mutein of claim 1, wherein the mutein has at least 90% identity to an amino acid sequence selected from the group consisting of SEQ ID NOs: 1-14.

11. The hNGAL mutein of claim 1, wherein the mutein is capable of binding angiopoietin-1 (Ang-1) with detectable affinity.

12. The hNGAL mutein of claim 11, wherein the mutein is capable of binding Ang-1 with an affinity measured by an IC50 value of about 150 nM or lower.

13. The hNGAL mutein of claim 11, wherein the mutein comprises a mutated amino acid residue at sixteen or more positions corresponding to positions 36, 40, 41, 49, 52, 65, 68, 70, 72-74, 77, 79, 81, 87, 96, 100, 103, 106, 116, 125, 126, 127, 129, 132, and 134 of the linear polypeptide sequence of mature hNGAL (SEQ ID NO: 16).

14. The hNGAL mutein of claim 11, wherein the mutein comprises an amino acid sequence selected from the group consisting of SEQ ID NOs: 1-14.

15. The hNGAL mutein of claim 11, wherein said mutein has at least 90% identity to an amino acid sequence selected from the group consisting of SEQ ID NOs: 1-14.

16. The hNGAL mutein of claim 1, wherein the mutein is cross-reactive with both human Ang-2 and mouse Ang-2.

17. The hNGAL mutein of claim 16, wherein the mutein is capable of binding mouse Ang-2 with an affinity measured by an IC50 value of about 5 nM or lower.

18. The hNGAL mutein of claim 1, wherein the mutein is capable of blocking the binding of human Ang-2 to human Tie-2 with an IC50 value of about 25 nM or lower.

19. The hNGAL mutein of claim 1, wherein the mutein comprises one or more non-native cysteine residues substituting one or more amino acids of mature hNGAL (SEQ ID NO: 16).

20. The hNGAL mutein of claim 19, wherein the mutein comprises at least one amino acid substitution of a native cysteine residue by another amino acid.

21. The hNGAL mutein of claim 20, wherein said another amino acid is a serine residue.

22. The hNGAL mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

23. The hNGAL mutein of claim 1, wherein the mutein is fused at its N-terminus and/or its C-terminus, with or without an intervening linker, to a fusion partner.

24. The hNGAL mutein of claim 23, wherein the fusion partner is selected from the group consisting of an antibody, an antibody fragment, a protein, a protein domain, a peptide, or a lipocalin mutein.

25. The hNGAL mutein of claim 1, wherein the mutein is conjugated to a compound that extends the serum half-life of the mutein.

26. The hNGAL mutein of claim 25, wherein the compound that extends the serum half-life is selected from the group consisting of a polyalkylene glycol molecule, hydroxyethyl starch, an Fc part of an immunoglobulin, a CH3 domain of an immunoglobulin, a CH4 domain of an immunoglobulin, an albumin binding peptide, and an albumin binding protein.

27. The hNGAL mutein of claim 26, wherein the polyalkylene glycol is polyethylene glycol (PEG) or an activated derivative thereof.

28. A pharmaceutical composition comprising an hNGAL mutein of claim 1.

29. The composition of claim 28, wherein the composition further includes at least one pharmaceutically acceptable adjuvant, diluent or carrier.

30. A composition comprising at least (a) an hNGAL mutein of claim 1 and (b) an anti-angiogenic agent.

31. The composition of claim 30, wherein the mutein and the anti-angiogenic agent are administered in combination, including concurrently, concomitantly or in series.

32. The composition of claim 30, wherein the mutein and the anti-angiogenic agent are administered independent from each other, including at individual intervals at independent points of time.

33. The composition of claim 30, wherein the anti-angiogenic agent is selected from the group consisting of: (i) antagonists of angiopoietin (Ang)-1, Ang-2, Ang-3, Ang-4, and/or Tie-2; (ii) antagonists of fms-like tyrosine kinase receptor 1 (Flt1), kinase insert domain-containing receptor (KDR), fms-like tyrosine kinase 4 (Flt4), vascular endothelial growth factor (VEGF)-A, VEGF-B, VEGF-C, VEGF-D, VEGF-E, placental growth factor (PlGF), and/or endocrine gland-derived VEGF (EG-VEGF); (iii) delta-like ligand 4 (DLL4, a vascular-specific Notch ligand) antagonists, (iv) epidermal growth factor receptor (EGFR) antagonists, and (v) cytokine inhibitors.

34. The composition of claim 30, wherein the anti-angiogenic agent is a VEGF inhibitor.

35. The composition of claim 34, wherein the VEGF inhibitor is selected from the group consisting of: VEGF-Trap, bevacizumab, sorafenib, sunitinib, and pazopanib.

36. The composition of claim 34, wherein the VEGF inhibitor is an antagonist of VEGF-A and/or an antagonist of VEGF-C.

37. The composition of claim 30, wherein the composition further comprises an additional anti-angiogenic agent.

38. The composition of claim 37, wherein the first anti-angiogenic agent is a VEGF-A antagonist and the second anti-angiogenic agent is a VEGF-C antagonist.

39. The composition of claim 38, wherein the antagonist of VEGF-A is an anti-VEGF-A antibody or a lipocalin mutein that has binding specificity for VEGF-A.

40. The composition of claim 38, wherein the antagonist of VEGF-C is an anti-VEGF-C antibody or a lipocalin mutein that has binding specificity for VEGF-C.

41. A diagnostic or analytical kit comprising an hNGAL mutein of claim 1.

42. A method of detecting the presence of Ang-2 in a sample, comprising the steps of (a) contacting the sample with an hNGAL mutein of claim 1 under conditions that allow the formation of a complex between the mutein and Ang-2, and (b) detecting the complex for the presence of Ang-2.

43. A method for the separation of Ang-2 in a sample, comprising the steps of (a) contacting the sample with an hNGAL mutein of claim 1 under conditions that allow the formation of a complex between the mutein and Ang-2, and (b) separating the complex from the sample.

44. A method of binding Ang-2 in a subject, comprising administering to said subject an hNGAL mutein of claim 1 or a composition comprising such mutein.

45. A method of inhibiting the binding of Ang-2 to Tie-2 in a subject, comprising administering to said subject an hNGAL mutein of claim 1 or a composition comprising such mutein.

46. A method of inhibiting or reducing angiogenesis in a subject, comprising administering to said subject an effective amount of an hNGAL mutein of claim 1 or a composition comprising such mutein.

47. A method of treating, or ameliorating a disease or disorder associated with deregulated angiogenesis in a subject wherein the disease or disorder is selected from the group consisting of: tumor growth, eye disorders, vascular diseases, inflammatory or infectious diseases, cancer, ocular neovascular diseases, arthritis and psoriasis, comprising administering to said subject an effective amount of an hNGAL mutein of claim 1 or a composition comprising such mutein.

* * * * *

SEQUENCE LISTING

<160> NUMBER OF SEQ ID NOS: 34

<210> SEQ ID NO 1
<211> LENGTH: 178
<212> TYPE: PRT
<213> ORGANISM: Artificial Sequence
<220> FEATURE:
<223> OTHER INFORMATION: hNGAL mutein

<400> SEQUENCE: 1

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Gln Ala Gly Asn Tyr Ile Leu Arg Glu Asp Lys Asp Pro
         35                  40                  45

Gly Lys Met Trp Ala Thr Ile Tyr Glu Leu Lys Glu Asp Lys Ser Tyr
     50                  55                  60

Asn Val Thr Gly Val Ser Phe Gly Pro Lys Lys Cys Asn Tyr Thr Ile
 65                  70                  75                  80

Trp Thr Phe Val Pro Gly Ser Gln Pro Gly Glu Phe Thr Leu Gly Gly
                 85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 2
<211> LENGTH: 178
<212> TYPE: PRT
<213> ORGANISM: Artificial Sequence
<220> FEATURE:
<223> OTHER INFORMATION: hNGAL mutein

<400> SEQUENCE: 2

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
             20                  25                  30

Val Val Gly Phe Ala Gly Asn His Arg Leu Arg Glu Asp Lys Asp Pro
         35                  40                  45

Gly Lys Met His Ala Thr Ile Tyr Glu Leu Lys Glu Asp Lys Ser Tyr
     50                  55                  60

Asn Val Thr Asp Val Thr Phe Ala Phe Lys Lys Cys Asn Tyr Arg Ile
 65                  70                  75                  80

His Thr Phe Val Pro Gly Ser Gln Pro Gly Glu Phe Thr Leu Gly Asn
                 85                  90                  95

Ile Lys Ser Trp Pro Gly Glu Thr Ser Thr Leu Val Arg Val Val Ser
            100                 105                 110
```

```
Thr Asn Tyr Asn Gln His Ala Met Val Phe Phe Lys Thr Val Met Gln
            115                 120                 125

Asn Arg Glu Trp Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: hNGAL mutein

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Trp Tyr Leu Arg Glu Asp Lys Asp Pro
            35                  40                  45

Ile Lys Met Thr Ala Thr Ile Tyr Glu Leu Lys Glu Asp Lys Ser Tyr
        50                  55                  60

Asn Val Thr Gln Val Gly Phe Glu Gln Lys Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Leu Leu Val Arg Val Val Ser
            100                 105                 110

Thr Asn Tyr Asn Gln His Ala Met Val Phe Phe Lys Gly Val Met Gln
        115                 120                 125

Asn Arg Glu Val Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: hNGAL mutein

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Glu Ala Gly Asn Val Glu Leu Arg Glu Asp Lys Asp Pro
            35                  40                  45
```

```
Val Lys Met Thr Ala Thr Ile Tyr Glu Leu Lys Glu Asp Lys Ser Tyr
 50                  55                  60

Asn Val Thr Glu Val Arg Phe Trp Leu Lys Cys Lys Tyr Asn Ile
 65                  70                  75                  80

His Thr Phe Val Pro Gly Ser Gln Pro Gly Glu Phe Thr Leu Gly Ala
                     85                  90                  95

Ile Lys Ser Gly Pro Gly Met Thr Ser Thr Leu Val Arg Val Val Ser
                100                 105                 110

Thr Asn Tyr Asn Gln His Ala Met Val Phe Phe Lys Thr Val Met Gln
                115                 120                 125

Asn Arg Glu Trp Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: hNGAL mutein

<400> SEQUENCE: 5

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Gln Ala Gly Asn Tyr Trp Leu Arg Glu Asp Lys Asp Pro
                 35                  40                  45

Ile Lys Met Ser Ala Thr Ile Tyr Glu Leu Lys Glu Asp Lys Ser Tyr
 50                  55                  60

Asn Val Thr Ile Val Tyr Phe Thr Arg Lys Lys Cys Ser Tyr Arg Ile
 65                  70                  75                  80

Tyr Thr Phe Val Pro Gly Ser Gln Pro Gly Glu Phe Thr Leu Gly Pro
                     85                  90                  95

Ile Lys Ser Tyr Pro Gly Asp Thr Ser Thr Leu Val Arg Val Val Ser
                100                 105                 110

Thr Asn Tyr Asn Gln His Ala Met Val Phe Phe Lys His Val Tyr Gln
                115                 120                 125

Asn Arg Glu Trp Phe Glu Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: hNGAL mutein
```

-continued

```
<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Glu Lys Met Trp Ala Thr Ile Tyr Glu Leu Lys Glu Asp Lys Ser Tyr
    50                  55                  60

Asp Val Thr Gly Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Ser Pro Gly Gln Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: hNGAL mutein

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Tyr Ile Leu Arg Glu Asp Lys Asp Pro
        35                  40                  45

Glu Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Asp Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

```
Leu Pro Glu Asn His Ile Val Phe Pro Val Pro Ile Asp Gln Cys Ile
                165                 170                 175

Asp Gly

<210> SEQ ID NO 8
<211> LENGTH: 178
<212> TYPE: PRT
<213> ORGANISM: Artificial Sequence
<220> FEATURE:
<223> OTHER INFORMATION: hNGAL mutein

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Tyr Ile Leu Arg Glu Asp Lys Asp Pro
            35                  40                  45

Gly Lys Met Trp Ala Thr Ile Tyr Glu Leu Lys Glu Asp Lys Ser Tyr
    50                  55                  60

Asp Val Thr Glu Val Ser Phe Gly Ala Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95

Ile Lys Ser Asp Pro Gly Gly Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: hNGAL mutein

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly His Ala Gly Asn Tyr Ile Leu Arg Glu Asp Lys Asp Pro
            35                  40                  45

Gly Lys Met Trp Ala Thr Ile Tyr Glu Leu Lys Glu Asp Lys Ser Tyr
    50                  55                  60

Asp Val Thr Glu Val Ser Phe Gly Pro Lys Lys Cys Asn Tyr Arg Ile
65                  70                  75                  80

Trp Thr Phe Val Pro Gly Ser Gln Pro Gly Glu Phe Thr Leu Gly Gly
                85                  90                  95
```

-continued

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: hNGAL mutein

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Tyr Ile Leu Arg Glu Asp Lys Asp Pro
        35                  40                  45

Gln Lys Met Trp Ala Thr Ile Tyr Glu Leu Lys Glu Asp Lys Ser Tyr
    50                  55                  60

Asp Val Thr Gly Val Ser Phe Gly Ala Lys Lys Cys Val Tyr Arg Ile
65                  70                  75                  80

Trp Thr Phe Val Pro Gly Ser Gln Pro Gly Glu Phe Thr Leu Gly Gly
                85                  90                  95

Ile Lys Ser Pro Pro Gly Gly Thr Ser Thr Leu Val Arg Val Val Ser
            100                 105                 110

Thr Asn Tyr Asn Gln His Ala Met Val Phe Phe Lys His Val Leu Gln
        115                 120                 125

Asn Arg Glu Phe Phe Glu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial Sequence
<220> FEATURE:
<223> OTHER INFORMATION: hNGAL mutein

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

-continued

```
Val Val Gly Gln Ala Gly Asn Tyr Ile Leu Arg Glu Asp Lys Asp Pro
             35                  40                  45

Val Lys Met Trp Ala Thr Ile Tyr Glu Leu Lys Glu Asp Lys Ser Tyr
 50                  55                  60

Asp Val Thr Glu Val Ser Phe Gly Pro Lys Lys Cys Asn Tyr Arg Ile
 65                  70                  75                  80

Trp Thr Phe Val Pro Gly Ser Gln Pro Gly Glu Phe Thr Leu Gly Gly
                 85                  90                  95

Ile Lys Ser Leu Pro Gly Gly Thr Ser Thr Leu Val Arg Val Val Ser
                100                 105                 110

Thr Asn Tyr Asn Gln His Ala Met Val Phe Phe Lys His Val Leu Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: Artificial Sequence
<220> FEATURE:
<223> OTHER INFORMATION: hNGAL mutein

<400> SEQUENCE: 12

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Val Ala Gly Asn Trp Tyr Leu Arg Glu Asp Lys Asp Pro
             35                  40                  45

Ile Lys Met Thr Ala Thr Ile Tyr Glu Leu Lys Glu Asp Lys Ser Tyr
 50                  55                  60

Asp Val Thr Gln Val Gly Phe Glu Gln Glu Lys Cys Lys Tyr Ser Ile
 65                  70                  75                  80

His Thr Phe Val Pro Gly Ser Gln Pro Gly Glu Phe Thr Leu Gly Asn
                 85                  90                  95

Ile Lys Ser Trp Pro Gly Asp Thr Ser Pro Leu Val Arg Val Val Ser
                100                 105                 110

Thr Asn Tyr Asp Gln His Ala Met Val Phe Phe Lys Gly Val Met Gln
            115                 120                 125

Asp Arg Glu Val Phe Ala Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 13
<211> LENGTH: 178
<212> TYPE: PRT
<213> ORGANISM: Artificial Sequence
```

```
<220> FEATURE:
<223> OTHER INFORMATION: hNGAL mutein

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Trp Tyr Leu Arg Glu Asp Lys Asp Pro
        35                  40                  45

Ile Lys Met Thr Ala Thr Ile Tyr Glu Leu Lys Glu Asp Lys Ser Tyr
50                  55                  60

Asp Val Thr Gln Val Gly Phe Glu Gln Glu Lys Cys Lys Tyr Ser Ile
65                  70                  75                  80

His Thr Phe Val Pro Gly Ser Gln Pro Gly Glu Phe Thr Leu Gly Asp
                85                  90                  95

Ile Lys Ser Trp Pro Gly Asp Thr Ser Pro Leu Val Arg Val Val Ser
            100                 105                 110

Thr Asn Tyr Asn Gln His Ala Met Val Phe Phe Lys Gly Met Met Gln
        115                 120                 125

Asp Arg Glu Val Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: Artificial Sequence
<220> FEATURE:
<223> OTHER INFORMATION: hNGAL mutein

<400> SEQUENCE: 14

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Trp Asp Leu Arg Glu Asp Lys Asp Pro
        35                  40                  45

Ile Lys Met Thr Ala Thr Ile Tyr Glu Leu Lys Glu Asp Lys Ser Tyr
50                  55                  60

Asp Val Thr Gln Val Ala Phe Glu Gln Lys Lys Cys Lys Tyr Ser Ile
65                  70                  75                  80

His Thr Phe Val Pro Gly Ser Gln Pro Gly Glu Phe Thr Leu Gly Gln
                85                  90                  95

Ile Lys Ser Trp Pro Gly Asp Thr Ser Pro Leu Val Arg Val Val Ser
            100                 105                 110

Thr Asn Tyr Asn Gln His Ala Met Val Phe Phe Lys Gly Val Met Gln
        115                 120                 125

Asn Arg Glu Val Phe Ala Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
                165                 170                 175

Asp Gly

<210> SEQ ID NO 15
<211> LENGTH: 10
<212> TYPE: PRT
<213> ORGANISM: Artificial Sequence
<220> FEATURE:
<223> OTHER INFORMATION: Strep-tag

<400> SEQUENCE: 15

Ser Ala Trp Ser His Pro Gln Phe Glu Lys
1               5                   10

<210> SEQ ID NO 16
<211> LENGTH: 178
<212> TYPE: PRT
<213> ORGANISM: Artificial Sequence
<220> FEATURE:
<223> OTHER INFORMATION: hNGAL wild-type

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 17
<211> LENGTH: 459
<212> TYPE: PRT
<213> ORGANISM: Artificial Sequence
<220> FEATURE:
<223> OTHER INFORMATION: benchmark antibody 1 heavy chain

<400> SEQUENCE: 17

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

```
Tyr Met His Trp Val Arg Gln Ala Pro Gly Gln Gly Leu Glu Trp Met
        35                  40                  45
Gly Trp Ile Asn Pro Asn Ser Gly Gly Thr Asn Tyr Ala Gln Lys Phe
 50                  55                  60
Gln Gly Arg Val Thr Met Thr Arg Asp Thr Ser Ile Ser Thr Ala Tyr
 65              70                  75                  80
Met Glu Leu Ser Arg Leu Arg Ser Asp Asp Thr Ala Val Tyr Tyr Cys
                 85                  90                  95
Ala Arg Ser Pro Asn Pro Tyr Tyr Asp Ser Ser Gly Tyr Tyr Tyr
                100                 105                 110
Pro Gly Ala Phe Asp Ile Trp Gly Gln Gly Thr Met Val Thr Val Ser
            115                 120                 125
Ser Ala Ser Thr Lys Gly Pro Ser Val Phe Pro Leu Ala Pro Ser Ser
    130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Gln
        195                 200                 205
Thr Tyr Ile Cys Asn Val Asn His Lys Pro Ser Asn Thr Lys Val Asp
    210                 215                 220
Lys Lys Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                245                 250                 255
Pro Lys Pro Lys Asp Thr Leu Met Ile Ser Arg Thr Pro Glu Val Thr
            260                 265                 270
Cys Val Val Val Asp Val Ser His Glu Asp Pro Glu Val Lys Phe Asn
        275                 280                 285
Trp Tyr Val Asp Gly Val Glu Val His Asn Ala Lys Thr Lys Pro Arg
    290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
            340                 345                 350
Gly Gln Pro Arg Glu Pro Gln Val Tyr Thr Leu Pro Pro Ser Arg Asp
        355                 360                 365
Glu Leu Thr Lys Asn Gln Val Ser Leu Thr Cys Leu Val Lys Gly Phe
    370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
            420                 425                 430
```

Asn Val Phe Ser Cys Ser Val Met His Glu Ala Leu His Asn His Tyr
            435                 440                 445

Thr Gln Lys Ser Leu Ser Leu Ser Pro Gly Lys
    450                 455

<210> SEQ ID NO 18
<211> LENGTH: 214
<212> TYPE: PRT
<213> ORGANISM: Artificial Sequence
<220> FEATURE:
<223> OTHER INFORMATION: benchmark antibody 1 light chain

<400> SEQUENCE: 18

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 19
<211> LENGTH: 452
<212> TYPE: PRT
<213> ORGANISM: Artificial Sequence
<220> FEATURE:
<223> OTHER INFORMATION: benchmark antibody 2 heavy chain

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
             85                  90                  95

Arg Gly Leu Ile Thr Phe Gly Gly Leu Ile Ala Pro Phe Asp Tyr Trp
         100                 105                 110

Gly Gln Gly Thr Leu Val Thr Val Ser Ser Ala Ser Thr Lys Gly Pro
     115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Lys Val Glu Pro Lys Ser
     210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
     290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Asp Glu Leu Thr Lys Asn Gln Val
         355                 360                 365

Ser Leu Thr Cys Leu Val Lys Gly Phe Tyr Pro Ser Asp Ile Ala Val
     370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
         435                 440                 445

Ser Pro Gly Lys
     450

<210> SEQ ID NO 20
<211> LENGTH: 214
<212> TYPE: PRT

<213> ORGANISM: Artificial Sequence
<220> FEATURE:
<223> OTHER INFORMATION: benchmark antibody 2 light chain

<400> SEQUENCE: 20

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Thr
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln His Tyr Asp Asn Ser Gln
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 21
<211> LENGTH: 536
<212> TYPE: DNA
<213> ORGANISM: Artificial Sequence
<220> FEATURE:
<223> OTHER INFORMATION: hNGAL mutein

<400> SEQUENCE: 21

```
caggactcca cctcagacct gatcccagcc ccacctctga gcaaggtccc tctgcagcag      60
aacttccagg acaaccaatt ccatgggaaa tggtatgtcg tgggccaagc cggaaattac     120
atcctgcgtg aggataagga tccgggaaaa atgtgggcga ccatttacga gttgaaagaa     180
gataaatcat ataacgtcac cggagtgagc tttggaccta agaaatgcaa ttacaccatt     240 tggaccttg tgccggggag ccagccgggc gagtttactt taggcggaat taaaagtcct      300
ccgggcggaa catcaacctt ggtccgcgtc gtgagcacca actacaacca gcatgccatg     360
gtgttcttca gcacgtgct gcagaaccgc gagttctttg atcacacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggcag         536
```

<210> SEQ ID NO 22
<211> LENGTH: 536
<212> TYPE: DNA
<213> ORGANISM: Artificial Sequence
<220> FEATURE:
<223> OTHER INFORMATION: hNGAL mutein

<400> SEQUENCE: 22

```
caggactcca cctcagacct gatcccagcc ccacctctga gcaaggtccc tctgcagcag    60
aacttccagg acaaccaatt ccatgggaaa tggtatgtcg tgggcttcgc cggaaatcac   120
cgtctgcgtg aggataagga tccgggaaaa atgcacgcga ccatttacga gttgaaagaa   180
gataaatcat ataacgtcac cgacgtgacc tttgcattca gaaatgcaa ttaccgtatt    240
cacacctttg tgccggggag ccagccgggc gagtttactt taggcaatat aaaagttgg    300
ccgggcgaga catcaacctt ggtccgcgtc gtgagcacca actacaacca gcatgccatg   360
gtgttcttca gaccgtgat gcagaaccgc gagtggtttt ggatcacact gtacgggcgc    420
acgaaagaac tgacaagcga gctgaaggaa aattttatcc gcttttccaa atctctgggc   480
ctccctgaaa accacatcgt cttccctgtc ccaatcgacc agtgtatcga cggcag       536
```

<210> SEQ ID NO 23
<211> LENGTH: 536
<212> TYPE: DNA
<213> ORGANISM: Artificial Sequence
<220> FEATURE:
<223> OTHER INFORMATION: hNGAL mutein

<400> SEQUENCE: 23

```
caggactcca cctcagacct gatcccagcc ccacctctga gcaaggtccc tctgcagcag    60
aacttccagg acaaccaatt ccatgggaaa tggtatgtcg tgggcgttgc cggaaattgg   120
tacctgcgtg aggataagga tccgatcaaa atgaccgcga ccatttacga gttgaaagaa   180
gataaatcat ataacgtcac ccaagtggga tttgagcaaa agaaatgcaa atacagcatt   240
cacacctttg tgccggggag ccagccgggc gagtttactt taggcgacat aaaagttgg    300
ccgggcgaca catcactgtt ggtccgcgtc gtgagcacca actacaacca gcatgccatg   360
gtgttcttca agggagtgat gcagaaccgc gaggttttttg caatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggcag       536
```

<210> SEQ ID NO 24
<211> LENGTH: 536
<212> TYPE: DNA
<213> ORGANISM: Artificial Sequence
<220> FEATURE:
<223> OTHER INFORMATION: hNGAL mutein

<400> SEQUENCE: 24

```
caggactcca cctcagacct gatcccagcc ccacctctga gcaaggtccc tctgcagcag    60
aacttccagg acaaccaatt ccatgggaaa tggtatgtcg tgggcgaggc cggaaatgtt   120
gagctgcgtg aggataagga tccggttaaa atgaccgcga ccatttacga gttgaaagaa   180
gataaatcat ataacgtcac cgaggtgcgt ttttggctga agaaatgcaa atacaatatt   240
cacacctttg tgccggggag ccagccgggc gagtttactt taggcgcaat taaaagtgga   300
ccgggcatga catcaacctt ggtccgcgtc gtgagcacca actacaacca gcatgccatg   360
gtgttcttca gaccgtgat gcagaaccgc gagtggtttt ggatcacact gtacgggcgc    420
```

```
acgaaagaac tgacaagcga gctgaaggaa aattttatcc gcttttccaa atctctgggc    480
ctccctgaaa accacatcgt cttccctgtc ccaatcgacc agtgtatcga cggcag        536
```

<210> SEQ ID NO 25
<211> LENGTH: 536
<212> TYPE: DNA
<213> ORGANISM: Artificial Sequence
<220> FEATURE:
<223> OTHER INFORMATION: hNGAL mutein

<400> SEQUENCE: 25

```
caggactcca cctcagacct gatcccagcc ccacctctga gcaaggtccc tctgcagcag     60
aacttccagg acaaccaatt ccatgggaaa tggtatgtcg tgggccaagc cggaaattac    120
tggctgcgtg aggataagga tccgatcaaa atgtctgcga ccatttacga gttgaaagaa    180
gataaatcat ataacgtcac catcgtgtac tttacccgta agaaatgcag ctaccgtatt    240
tacacctttg tgccggggag ccagccgggc gagtttactt taggccctat taaaagttac    300
ccgggcgaca catcaacctt ggtccgcgtc gtgagcacca actacaacca gcatgccatg    360
gtgttcttca gcacgtgta ccagaaccgc gagtggtttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggcag        536
```

<210> SEQ ID NO 26
<211> LENGTH: 535
<212> TYPE: DNA
<213> ORGANISM: Artificial Sequence
<220> FEATURE:
<223> OTHER INFORMATION: hNGAL mutein

<400> SEQUENCE: 26

```
caggactcca cctcagacct gatcccagcc ccacctctga gcaaggtccc tctgcagcag     60
aacttccagg acaaccaatt ccatgggaaa tggtacgtag ttgggcaggc cggaaattat    120
attctgcgtg aggataagga tccggagaaa atgtgggcga ccatttacga gttgaaagaa    180
gataaatcat atgacgtcac cggggtgtcg tttgggccta agaaatgcaa ttacaggatt    240
tggacctttg tgccggggag ccagccgggc gagtttactt taggcgggat taaaagttct    300
ccgggccaga catcaacgtt ggtccgcgtc gtgagcacca actacaacca gcatgccatg    360
gtgttcttca gcatgtgct tcagaaccgc gagttttttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggca         535
```

<210> SEQ ID NO 27
<211> LENGTH: 536
<212> TYPE: DNA
<213> ORGANISM: Artificial Sequence
<220> FEATURE:
<223> OTHER INFORMATION: hNGAL mutein

<400> SEQUENCE: 27

```
caggactcca cctcagacct gatcccagcc ccacctctga gcaaggtccc tctgcagcag     60
aacttccagg acaaccaatt ccatgggaaa tggtacgtag ttgggcatgc cggaaattat    120
attctgcgtg aggataagga tccggagaaa atgtgggcga ccatttacga gttgaaagaa    180
gataaatcat atgacgtcac cgaggtgtct tttgggccga agaaatgcaa ttacaggatt    240
tggacctttg tgccggggag ccagccgggc gagtttactt taggcggtat taaaagtcct    300
```

```
ccgggcgata catcaacgtt ggtccgcgtc gtgagcacca actacaacca gcatgccatg    360
gtgttcttca agcatgtgct tcagaaccgc gagttttttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggcag        536

<210> SEQ ID NO 28
<211> LENGTH: 536
<212> TYPE: DNA
<213> ORGANISM: Artificial Sequence
<220> FEATURE:
<223> OTHER INFORMATION: hNGAL mutein

<400> SEQUENCE: 28
caggactcca cctcagacct gatcccagcc ccacctctga gcaaggtccc tctgcagcag    60
aacttccagg acaaccaatt ccatgggaaa tggtacgtag ttgggcaggc cggaaattat    120
attctgcgtg aggataagga tccggggaaa atgtgggcga ccatttacga gttgaaagaa    180
gataaatcat atgacgtcac cgaggtgtcg tttgggccta agaaatgcaa ttacaggatt    240 tggaccttg tgccggggag ccagccgggc gagtttactt taggcggtat taaaagtgat    300
ccgggcggga catcaacgtt ggtccgcgtc gtgagcacca actacaacca gcatgccatg    360
gtgttcttca agcatgtgct tcagaaccgc gagttttttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggcag        536

<210> SEQ ID NO 29
<211> LENGTH: 536
<212> TYPE: DNA
<213> ORGANISM: Artificial Sequence
<220> FEATURE:
<223> OTHER INFORMATION: hNGAL mutein

<400> SEQUENCE: 29
caggactcca cctcagacct gatcccagcc ccacctctga gcaaggtccc tctgcagcag    60
aacttccagg acaaccaatt ccatgggaaa tggtacgtag ttgggcatgc cggaaattat    120
attctgcgtg aggataagga tccggggaaa atgtgggcga ccatttacga gttgaaagaa    180
gataaatcat atgacgtcac cgaggtgtct tttgggccta agaaatgcaa ttaccgtatt    240 tggaccttg tgccggggag ccagccgggc gagtttactt taggcggtat taaaagtccg    300
ccgggcggga catcaacgtt ggtccgcgtc gtgagcacca actacaacca gcatgccatg    360
gtgttcttca agcatgtgct tcagaaccgc gagttttttg agatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggcag        536

<210> SEQ ID NO 30
<211> LENGTH: 535
<212> TYPE: DNA
<213> ORGANISM: Artificial Sequence
<220> FEATURE:
<223> OTHER INFORMATION: hNGAL mutein

<400> SEQUENCE: 30
caggactcca cctcagacct gatcccagcc ccacctctga gcaaggtccc tctgcagcag    60
aacttccagg acaaccaatt ccatgggaaa tggtacgtag ttgggcaggc cggaaattat    120
```

```
attctgcgtg aggataagga tccgcagaaa atgtgggcga ccatttacga gttgaaagaa      180
gataaatcat atgacgtcac cggtgtgtct tttggggcta agaaatgcgt ttacaggatt      240
tggacctttg tgccggggag ccagccgggc gagtttactt taggcggtat taaaagtccg      300
ccgggcggta catcaacgtt ggtccgcgtc gtgagcacca actacaacca gcatgccatg      360
gtgttcttca agcatgtgct tcagaaccgc gagttttttg agatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggca           535
```

<210> SEQ ID NO 31
<211> LENGTH: 536
<212> TYPE: DNA
<213> ORGANISM: Artificial Sequence
<220> FEATURE:
<223> OTHER INFORMATION: hNGAL mutein

<400> SEQUENCE: 31

```
caggactcca cctcagacct gatcccagcc ccacctctga gcaaggtccc tctgcagcag      60
aacttccagg acaaccaatt ccatgggaaa tggtacgtag ttgggcaggc cggaaattat     120
attctgcgtg aggataagga tccggttaaa atgtgggcga ccatttacga gttgaaagaa     180
gataaatcat atgacgtcac cgaggtgtct tttggtccta gaaatgcaa ttacaggatt      240 tggacctttg tgccggggag ccagccgggc gagtttactt taggcgggat taaaagtctt     300
ccgggcggta catcaacttt ggtccgcgtc gtgagcacca actacaacca gcatgccatg     360
gtgttcttca agcatgtgct tcagaaccgc gagttttttg agatcacact gtacgggcgc    420
acgaaagaac tgacaagcga gctgaaggaa aattttatcc gcttttccaa atctctgggc     480
ctccctgaaa accacatcgt cttccctgtc ccaatcgacc agtgtatcga cggcag          536
```

<210> SEQ ID NO 32
<211> LENGTH: 535
<212> TYPE: DNA
<213> ORGANISM: Artificial Sequence
<220> FEATURE:
<223> OTHER INFORMATION: hNGAL mutein

<400> SEQUENCE: 32

```
caggactcca cctcagacct gatcccagcc ccacctctga gcaaggtccc tctgcagcag      60
aacttccagg acaaccaatt ccatgggaaa tggtatgtcg tgggcgttgc cggaaattgg     120
tacctgcgtg aggataagga tccgatcaaa atgaccgcga ccatttacga gttgaaagaa     180
gataaatcat atgacgtcac ccaagtggga tttgagcaag agaaatgcaa atacagcatt     240
cacacctttg tgccggggag ccagccgggc gagtttactt taggcaacat taaaagttgg     300
ccgggcgaca catcaccgtt ggtccgcgtc gtgagcacca actacgacca gcatgccatg     360
gtgttcttca agggagtgat gcaggatcgc gaggtttttg caatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggca           535
```

<210> SEQ ID NO 33
<211> LENGTH: 535
<212> TYPE: DNA
<213> ORGANISM: Artificial Sequence
<220> FEATURE:
<223> OTHER INFORMATION: hNGAL mutein -continued

```
<400> SEQUENCE: 33
caggactcca cctcagacct gatcccagcc ccacctctga gcaaggtccc tctgcagcag      60
aacttccagg acaaccaatt ccatgggaaa tggtatgtcg tgggcgttgc cggaaattgg     120
tacctgcgtg aggataagga tccgatcaaa atgaccgcga ccatttacga gttgaaagaa     180
gataaatcat atgacgtcac ccaagtggga tttgagcaag agaaatgcaa atacagcatt     240
cacacctttg tgccggggag ccagccgggc gagtttactt taggcgacat taagagttgg     300
ccgggcgaca catcaccgtt ggtccgcgtc gtgagcacca actacaacca gcatgccatg     360
gtgttcttca agggaatgat gcaggaccgc gaggttttg caatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggca          535

<210> SEQ ID NO 34
<211> LENGTH: 535
<212> TYPE: DNA
<213> ORGANISM: Artificial Sequence
<220> FEATURE:
<223> OTHER INFORMATION: hNGAL mutein

<400> SEQUENCE: 34
caggactcca cctcagacct gatcccagcc ccacctctga gcaaggtccc tctgcagcag      60
aacttccagg acaaccaatt ccatgggaaa tggtacgtag taggtatggc cggaaattgg     120
gatctgcgtg aggataagga tccgattaaa atgacggcga ccatttacga gttgaaagaa     180
gataaatcat atgacgtcac ccaggtggcg tttgagcaga agaaatgcaa gtactcgatt     240
catacctttg tgccggggag ccagccgggc gagtttactt taggccagat taaaagttgg     300
ccgggcgata catcaccttt ggtccgcgtc gtgagcacca actacaacca gcatgccatg     360
gtgttcttca aggggtgat gcagaaccgc gaggtgtttg ctatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggca          535
```